United States Patent [19]

Mizuno et al.

[11] Patent Number: 5,416,082
[45] Date of Patent: * May 16, 1995

[54] PYRROLOAZEPINE DERIVATIVES

[75] Inventors: Akira Mizuno, Kyoto; Hidetsura Cho, Kitakasugaoka; Mikiko Hamaguchi, Kawanishi; Toshio Tatsuoka, Nishinomiya; Takafumi Ishihara, Takatsuka, all of Japan

[73] Assignee: Suntory Limited, Osaka, Japan

[*] Notice: The portion of the term of this patent subsequent to Jun. 25, 2008 has been disclaimed.

[21] Appl. No.: 195,019

[22] Filed: Feb. 14, 1994

Related U.S. Application Data

[60] Continuation of Ser. No. 987,703, Dec. 9, 1992, which is a division of Ser. No. 651,778, Feb. 7, 1991, Pat. No. 5,206,239.

[30] Foreign Application Priority Data

Feb. 7, 1990 [JP] Japan .................................. 2-26137
Jan. 30, 1991 [JP] Japan .................................. 3-027739

[51] Int. Cl.$^6$ ...................... A61K 31/55; C07D 487/04
[52] U.S. Cl. ...................................... 514/215; 540/521
[58] Field of Search ........................ 540/521; 514/215

[56] References Cited

U.S. PATENT DOCUMENTS

| | | | |
|---|---|---|---|
| 3,563,979 | 2/1971 | Hester | 260/239.3 |
| 3,573,323 | 3/1971 | Hester | 260/326.5 |
| 3,573,324 | 3/1971 | Hester | 260/320.5 |
| 5,206,239 | 4/1993 | Mizuno et al. | 540/521 |

FOREIGN PATENT DOCUMENTS

| | | |
|---|---|---|
| 3903368 | 8/1990 | Germany . |
| 62-161786 | 7/1987 | Japan . |
| 2-500738 | 3/1990 | Japan . |

OTHER PUBLICATIONS

Journal of Natural Products, vol. 48, No. 1, pp. 47-53, Jan.-Feb. 1985, F. J. Schmitz, et al., "Marine Natural Products: Pyrrololactams from Several Sponges".

Journal of the Chemical Society, Jan. 3, 1980, pp. 435-436, G. Sharma, et al., "Characterization of a Yellow Compound Isolated from the Marine Sponge Phakellia Flabellata".

Tetrahedron, vol. 41, No. 24, pp. 6019-6033, 1985, G. De Nanteuil, et al., "Invertebres Marins du Lagon Neo-Caledonien-V1", (with English Abstract).

Chemical Abstracts, vol. 102, 1985, AM-146334h, N. K. Utkina, et al., "Nitrogen-Containing Metabolites of the Marine Sponge *Acanthella carteri*".

Aust. J. Chem., vol. 43, 1990, pp. 355-365, B. Kasum, et al., "Dihydroindol-7(6H)-ones and 6,7-Dihydropyrrolo[2,3-c]azepine-4,8(1H,5H)-dione".

Primary Examiner—Mukund J. Shah
Assistant Examiner—Pavanaram K. Sripada
Attorney, Agent, or Firm—Oblon, Spivak, McClelland, Maier & Neustadt

[57] ABSTRACT

Disclosed herein are pyrroloazepine derivatives having anti-$\alpha_1$ activity and anti-serotonin activity represented by the following formula (I):

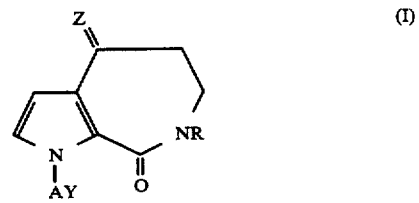

wherein R means a hydrogen atom, a linear or branched $C_{1-6}$ alkyl group or a $C_{7-10}$ aralkyl group, A denotes a linear or branched $C_{2-10}$ alkylene, alkenylene or alkynylene group, Z stands for O, $NOR_1$ or $NOCOR_5$ in which $R_1$ and $R_5$ is a hydrogen atom or an alkyl, aryl or aralkyl group, and Y means a particular piperidinyl or pyrrolidinyl group; and salts thereof. Their preparation processes are also disclosed.

9 Claims, No Drawings

PYRROLOAZEPINE DERIVATIVES

This is a Continuation Application of application Ser. No. 07/987,703 filed Dec. 9, 1992 which is a divisional of Ser. No. 07/651,778 filed Feb. 7, 1991, now U.S. Pat. No. 5,206,239.

BACKGROUND OF THE INVENTION

1. Field of the Invention

The present invention relates to novel pyrroloazepine derivatives, and more specifically to novel pyrroloazepine derivatives and salts thereof, said derivatives and salts having strong anti-$\alpha_1$ action and anti-serotonin action but low toxicity and being useful as therapeutics for circulatory diseases such as hypertension and congestive heart failure, their preparation processes thereof and therapeutics for circulatory diseases, said therapeutics containing them as active ingredients.

2. Description of the Prior Art

Numerous substances have heretofore been known as drugs which act on the circulatory system. Among these, a variety of substances have been developed as antihypertensive drugs.

Of such antihypertensive drugs, $\alpha_1$-blockers represented by prazosin have such merits that (1) their antihypertensive action is strong and sure, (2) they do not give adverse influence to the lipidometabolic and glycometabolic systems and (3) they can be easily used for hypertensives having complication. Their development is hence actively under way. Clinically-applied examples of such $\alpha_1$-blockers include bunazosin, doxazosin, terazosin and urapidil in addition to prazosin.

$\alpha_1$-Blockers are however accompanied by the drawback that they generally have side effects such as orthostatic disorder and reflex tachycardia, tend to induce orthostatic hypotension especially when administered to aged people and hence require attention.

As a drug having less tendency of inducing such side effects of $\alpha_1$-blockers, ketanserin having both anti-serotonin action and anti-$\alpha_1$ action has been developed as a drug effective for senile hypertension and the like.

However, this ketanserin may not be able to exhibit, for example, sufficient hypotensive action in some instances, and its side effects to the central nervous system such as drowsiness and sedative action have posed problems.

SUMMARY OF THE INVENTION

In view of the foregoing circumstances, the present inventors synthesized numerous compounds and investigated their pharmacological effects with a view toward obtaining drugs having both anti-serotonin action and anti-$\alpha_1$ action, strong hypertensive action, and low side effects and toxicity.

As a result, the compounds represented by the below-described formula (I) having the pyrroloazepine structure have been found to meet the above requirements, leading to the completion of the present invention.

This invention therefore provides a pyrroloazepine derivative represented by the following formula (I):

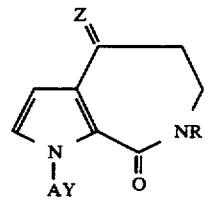

wherein R means a hydrogen atom, a linear or branched $C_{1-6}$ alkyl group or a $C_{7-10}$ aralkyl group, A denotes a linear or branched $C_{2-10}$ alkylene, alkenylene or alkynylene group, Z stands for O, $NOR_1$ in which $R_1$ is a hydrogen atom or an alkyl, aryl or aralkyl group, or $NOCOR_5$ in which $R_5$ is a hydrogen atom or an alkyl, aryl or aralkyl group, and Y means a group

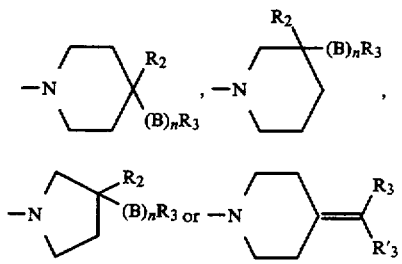

in which $R_2$ means a hydrogen atom or a cyano group, $R_3$ an $R'_3$ may be the same or different and individually denote a substituted or unsubstituted phenyl group or a substituted or unsubstituted aralkyl group, and B is an oxygen or sulfur atom or a carbonyl, substituted or unsubstituted hydroxymethylene, sulfinyl, sulfonyl or substituted or unsubstituted, cyclic or acyclic acetal, and n stands for 0 or 1, or a salt thereof; a preparation process thereof: and a therapeutic for circulatory diseases, said therapeutic comprising as active ingredient the pyrroloazepine derivative or the salt thereof.

The pyrroloazepine derivatives (I) and their pharmacologically acceptable salts according to the present invention are drugs having anti-$\alpha_1$ action and anti-serotonin action and have a high degree of safety. They can therefore be used, for example, as novel therapeutics for circulatory diseases.

DETAILED DESCRIPTION OF THE INVENTION AND PREFERRED EMBODIMENTS

In the pyrroloazepine derivative (I) of the present invention, preferred examples of group A include $C_{3-6}$ alkenyl groups such as —$CH_2CH$=$CHCH_2$—, $C_{3-6}$ alkynyl groups such as $CH_2C$≡$CCH_2$—, and $(CH_2)_n$ (n: 3–5). Preferred examples of group R include hydrogen atom, and methyl, ethyl, propyl, isopropyl, butyl, isobutyl, t-butyl, pentyl and benzyl groups. In addition, preferred examples of $R_3$ and $R_3'$ include a phenyl group; a phenyl group substituted by one or more halogen atoms such as fluorine, chlorine and bromine, and $C_{1-4}$ alkoxy groups such as methoxy and ethoxy groups; a benzyl group; and a diphenylmethyl group. When $R_3$ and $R_3'$ mean substituted aralkyl groups, each substituent may be bonded to either the aryl moiety or the alkyl moiety. When B stands for a substituted hydroxymethylene group, exemplary substituents include lower alkyl groups such as methyl, ethyl and propyl; a phenyl group; and a phenyl group substituted by one or more halogen atoms such as fluorine, chlorine and bromine and $C_{1-4}$ alkoxy groups such as methoxy and ethoxy groups. Further, examples of the substituted or unsubstituted, cyclic or acyclic acetal represented by B include

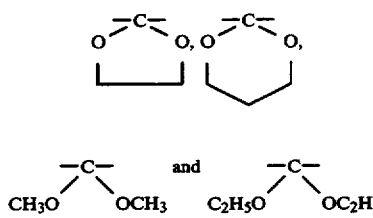

In addition, preferred examples of group $R_1$ include hydrogen atom, lower alkyl groups such as methyl group, and $C_{7-10}$ aralkyl groups such as benzyl group. Preferred examples of $R_5$ include lower alkyl groups such as methyl groups and aryl groups such as phenyl group.

Where compounds according to the present invention have isomers, it is to be noted that these isomers are all embraced by the present invention. For example, when there is a hydroxyimino group or an O-substituted hydroxyimino group at 4-position of the pyrroloazepine ring, there are both an (E)-isomer and a (Z) isomer with respect to the group. The compounds of the present invention also include these individual isomers and their mixtures.

The pyrroloazepine derivatives (I) according to the present invention can be prepared by a desired conventional method. However, the pyrroloazepine derivatives (I) are preferably prepared, for example, by any of the following processes:

(1) Among the pyrroloazepine derivatives (I), the compounds (Ia) in which Z represents O can each be obtained in accordance with the following reaction scheme, namely, by converting the compound represented by formula (II) to the compound represented by formula (III) and then reacting the nitrogen-containing cyclic compound represented by formula (IV) or a salt thereof with the compound (III).

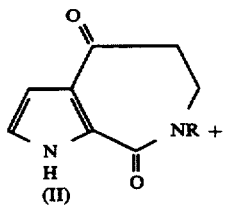

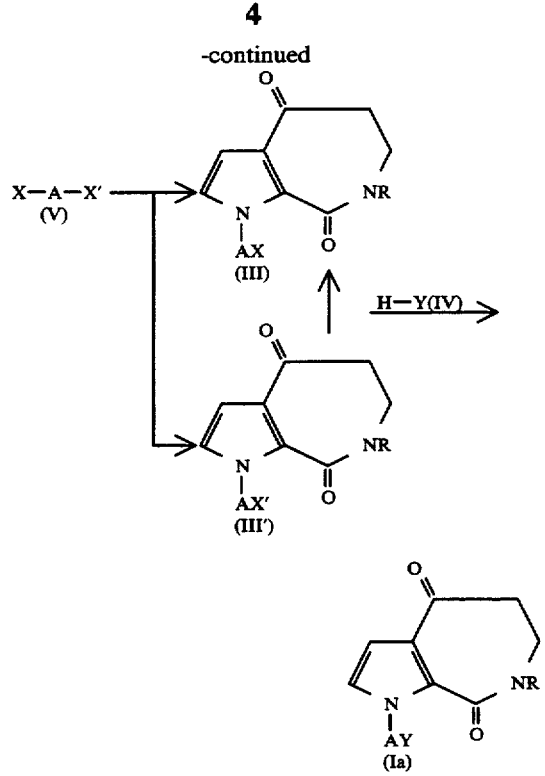

wherein A, R and Y have the same meanings as defined above, X means a substituent easily replaceable with an amino group, and X' denotes a hydroxyl group or a substituent easily replaceable with an amino group.

The conversion from the compound (II) to the compound (III) is effected by causing the compound represented by formula (V) to act on the compound (II) in the presence of an organic or inorganic base. Examples of the substituent, which is easily replaceable with an amino group, as group X in the compound (V) include halogen atoms such as chlorine and bromine atoms, methanesulfonyl group and p-toluenesulfonyl group. Any solvent can be used in this reaction as long as it does not take part in the reaction. Illustrative solvents include dimethylformamide, acetonitrile, dimethylsulfoxide, tetrahydrofuran, dioxane and acetone. Further, exemplary organic or inorganic bases include triethylamine, pyridine, collidine, 1,8-diazabicyclo[5.4.0]undec-7-ene (DBU), sodium hydroxide, potassium hydroxide, sodium carbonate, potassium carbonate, sodium ethoxide, and potassium t-butoxide. The reaction is conducted at $-20°$ C. to the reflux temperature.

To prepare the compound (Ia) by reacting the compound (III) with the nitrogen-containing cyclic compound (IV), it is only necessary to react at room temperature to 150° C. the nitrogen-containing cyclic compound (IV) or an organic acid or inorganic acid salt thereof with the compound (III), optionally together with an organic base such as triethylamine, pyridine, collidine, DBU or potassium t-butoxide or an inorganic base such as potassium carbonate, sodium carbonate, potassium hydroxide or sodium hydroxide, optionally after adding an iodide such as sodium iodide or potassium iodide.

Examples of the nitrogen-containing cyclic compound (IV) include 4-phenylpiperidine, 4-benzylpiperidine, 4-[bis(4-fluorophenyl)methylene]piperidine, α,α- bis-(4-fluorophenyl)-4-piperidinemethanol, 4-(diphenylmethoxy)piperidine, 4-cyano-4-phenylpiperidine, 4-(4-fluorobenzoyl)piperidine, 4-benzoylpiperidine, 4-(4-methoxybenzoyl)piperidine, 4-(4-chlorobenzoyl)piperidine, 3-(4-fluorobenzoyl)piperidine, 3-benzoylpyrrolidine, 3-(4-fluorobenzoyl)pyrrolidine, 4-(4-fluorophenoxy)piperidine, 4-[(4-fluorophenyl)thio]piperidine, 4-[(4-fluorophenyl)sulfinyl]piperidine, 4-[(4-fluorophenyl)sulfonyl]piperidine, and 4-(4-fluorobenzoyl)-piperidine ethyleneacetal. They are all either known compounds or compounds which can be readily prepared by a known process or a process similar to the known process.

Incidentally, among the compounds (II) employed as starting materials in the above reaction, the compound in which R is H has been known but the remaining compounds are novel compounds. These novel compounds can each be prepared in accordance with the following reaction scheme, namely, by reacting a pyrrole-2-carboxylic acid or a derivative thereof represented by the formula (VI) with a β-amino acid or a derivative therof represented by the formula (VII) or an organic or inorganic salt of the β-amino acid or the derivative thereof and optionally removing the protecting group, thereby obtaining the compound represented by the formula (VIII) and then ring-closing this compound.

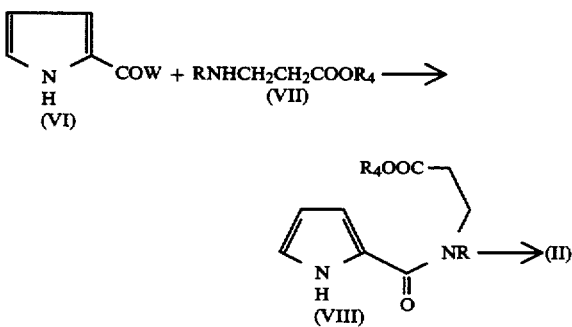

wherein R has the same meaning as defined above, $R_4$ means a hydrogen atom or a carboxyl-protecting group, and W denotes a hydroxyl group or a substituent easily replaceable with an amino group.

Examples of the substituent easily replaceable with an amino group as represented by W in the compound (VI) include halogen atoms, carboxylic acid residue and the like. On the other hand, as the carboxyl-protecting group, it is possible to use, in addition to lower alkyl groups such as methyl, ethyl, propyl, isopropyl, n-butyl, isobutyl and t-butyl and $C_{7-20}$ aralkyl groups such as benzyl and 9-anthrylmethyl, the conventional protecting groups described by T. W. Greene in "Protective Groups in Organic Synthesis" (John Wiley & Sons, Inc.) and the like. For the synthesis of the compounds (VIII), it is possible to use any one of the various processes disclosed in "Compendium for Organic Synthesis" (WILEY-INTERSCIENCE, a division of John Wiley & Sons, Inc.) and the like. Exemplary processes include the process in which pyrrole-2-carboxylic acid of the compound (VI) in which W is OH is treated with an organic compound such as diethyl cyanophosphonate (DEPC), diphenylphosphoryl azide (DPPA), dicyclohexylcarbodiimide (DCC), 1-ethyl-3-(3-dimethylaminopropyl)carbodiimide hydrochloride or 2-iodo-1-methylpyridinium iodide or an inorganic compound such as silicon tetrachloride or tin tetrachloride, if necessary, in the presence of an organic or inorganic base; and the process in which pyrrole-2-carboxylic acid is reacted after converting it to its acid halide, symmetric acid anhydride, mixed acid anhydride or its active ester such as p-nitrophenyl ester or to a like compound.

Each compound (VIII) thus obtained is subjected to a cyclizing reaction, optionally after removing the protecting group by virtue of a suitable method such as the action of an acid or a base, or catalytic reduction. This cyclizing reaction is conducted by treating the compound (VIII) together with an organic acid such as methanesulfonic acid, an inorganic acid such as sulfuric acid or polyphosphoric acid or a mixture of such an organic or inorganic acid and diphosphorus pentoxide at room temperature to 170° C., preferably at 80°–120° C. In this case, a solvent which does not take part in the reaction may be added as needed. As an alternative, the cyclizing reaction can also be practiced by treating the compound (VIII) with oxalyl chloride, thionyl chloride, thionyl bromide, oxalyl bromide, phosgene, phosphorus trichloride, phosphorus tribromide, phosphoryl chloride, phosphoryl bromide or the like, optionally in the presence of a catalyst to convert the compound (VIII) to its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane or heating the acid halide in acetic acid.

The compounds (II) obtained in the above manner can be used directly as starting materials for the preparation of the compounds (Ia) of the present invention. They can also be used after purification by a conventional purification method, for example, by recrystallization or column chromatography if necessary.

(2) Among the pyrroloazepine derivatives (I), the compounds (Ib) in which Z is represented by $NOR_1$ can each be prepared in accordance with the following reaction formula, namely, (i) by causing a hydroxylamine or a derivative therof represented by the formula (IX) or or a salt of the hydroxylamine or the derivative to act on the compound (Ia) obtained by the above-described reaction or (ii) by causing the hydroxylamine or its derivative (IX) or a salt of the hydroxylamine or the derivative to act on the compound (III) and then causing a nitrogen-containing cyclic compound (IV) or a salt thereof to act further.

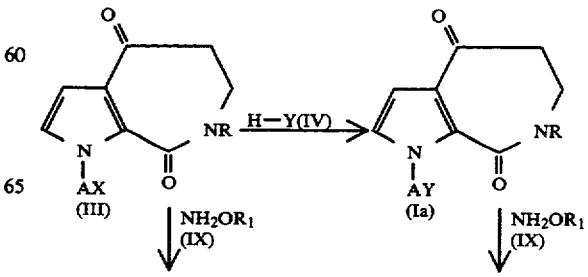

-continued

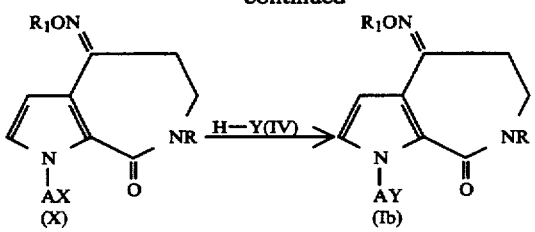

wherein A, R, R₁, X and Y have the same meanings as defined above.

The reaction between the compound (Ia) or (III) and the hydroxylamine or its derivative (IX) is practiced, if necessary, in the presence of an organic base such as pyridine, triethylamine, collidine, DBU or sodium acetate or an inorganic base such as potassium carbonate or sodium hydroxide. The hydroxylamine or its derivative (IX) may also be used in the form of an organic acid salt or an inorganic acid salt.

The compound (X) obtained by the reaction of the compound (III) with the compound (IX) can be reacted further with the nitrogen-containing cyclic compound (IV) by the method described above, whereby the compound (X) can be converted to the compound (Ib).

Upon preparation of the compound (Ib), it is determined depending on the structure and properties of the nitrogen-containing cyclic compound (IV) whether the hydroxylamine or its derivative (IX) should be reacted to the compound (III) or to the compound (Ia). Where there is a group reactive to the hydroxylamine or its derivative (IX), such as a carbonyl group, in the nitrogen-containing cyclic compound (IV), it is desirable to choose the process that the hydroxylamine or its derivative (IX) is reacted to the compound (III).

(3) Among the pyrroloazepine derivatives (I), the compounds (Ic) in which X is represented by

can each be prepared (i) by acylating the compound (Ib') [i.e., the compound of formula (Ib) in which R₁ is H)], which has been obtained by the above reaction formula, with a carboxylic acid or its derivative represented by formula (XI) or (ii) by acylating the compound (X') [i.e., the compound of formula (X) in which R₁ is H)] with a carboxylic acid or its derivative represented by formula (XI) and then causing a nitrogen-containing cyclic compound (IV) or its salt to act further.

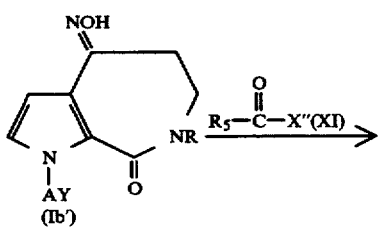

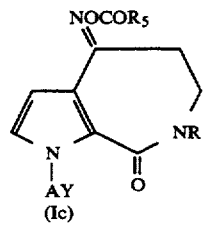

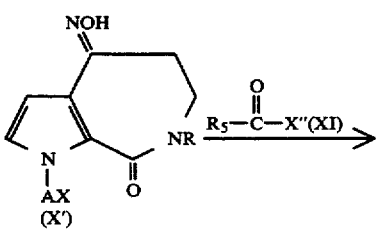

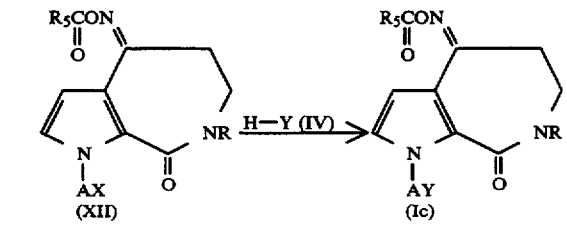

wherein A, R, X and Y have the same meanings as defined above, R₅ means a hydrogen atom or an alkyl, aryl or aralkyl group, and X″ denotes a hydroxyl group or an eliminative substituent easily reactable with a hydroxyimino group.

Illustrative of the eliminative group (X″) easily reactable with a hydroxyimino group include cyano group, halogen atoms such as Cl and Br, p-nitrophenoxy group, and those represented by the formula

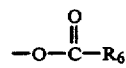

wherein R₆ means an alkyl, aryl, aralkyl, alkoxyl or aryloxyl group.

The reaction between the compound (Ib') or (X') with the carboxylic acid or its derivative represented by the formula (XI) can be conducted using any one of the various esterification processes described in "Compendium of Organic Synthetic Methods" (WILEY-INTERSCIENCE, a division of John Wiley & Sons, Inc.) and the like.

Examples include the process in which the compound (Ib') or (X') and the carboxylic acid represented by the formula (XI') [the compound of formula (XI) in which X″ is OH] are condensed with diethyl cyanophosphonate (DEPC), diphenylphosphoryl azide (DPPA), dicyclohexylcarbodiimide (DCC), 1-ethyl-3-(3-dimethylaminopropyl)carbodiimide hydrochloride, 2-iodo-1-methylpyridinium iodide or the like, if necessary in the presence of an organic base such as triethylamine, pyridine, collidine, DBU or sodium acetate or an inorganic base such as potassium carbonate or sodium hydroxide; and the process in which the acid halide represented by the formula (XI″) [the compound of (XI) in which X″ is a halogen atom such as chlorine or bromine] is reacted to the compound (Ib') or (X'), if necessary in the presence of the above-described organic or inorganic base.

If necessary, the compounds (I) of the present invention obtained as described above can be reacted with various acids or alkylating or aralkylating agent to convert the compounds (I) to their pharmacologically acceptable salts, followed by purification by recrystallization or column chromatography and the like.

Exemplary acids usable to convert the pyrroloazepine derivatives (I) to their salts include inorganic acids such as hydrochloric acid, nitric acid, sulfuric acid, phosphoric acid and hydrobromic acid; and organic acids such as maleic acid, fumaric acid, tartaric acid, oxalic acid, lactic acid, citric acid, acetic acid, methanesulfonic acid, p-toluenesulfonic acid, adipic acid, palmitic acid and tannic acid.

In addition, other exemplary salts of the compounds (I) of the present invention include their quaternary ammonium salts, which are obtained by causing an alkylating agent. Usable examples of the alkylating agent include $C_{1-10}$ alkyl halides, $C_{7-12}$ aralkyl halides, dialkyl sulfates and the like. Exemplary $C_{1-10}$ alkyl halides include methyl chloride, ethyl chloride, methyl bromide, ethyl bromide, methyl iodide and ethyl iodide and exemplary $C_{7-12}$ aralkyl halides include benzyl chloride and benzyl bromide, while illustrative dialkyl sulfates include dimethyl sulfate and diethyl sulfate.

The pyrroloazepine derivatives (I) and their salts, which are obtained as described above, have anti-$\alpha_1$ action and anti-serotonin action as will be demonstrated later by tests. Further, their $LD_{50}$ values are as high as at least 300 mg/kg (p.o) so that they have a high degree of safety. The compounds according to the present invention can therefore be used as therapeutics for circulatory diseases such as hypertension and congestive heart failure.

When the pyrroloazepine derivatives (I) and their salts are used as drugs, they can be administered in an effective dose as they are. As an alternative, they can also be formulated into various preparation forms by known methods and then administered.

Exemplary preparation forms as drugs include orally administering preparation forms such as tablets, powders, granules, capsules and syrups as well as parenterally administering preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth, magnesium stearate, talc, polyethylene glycol, polyvinyl alcohol, silica, lactose sugar, crystalline cellulose, starch, calcium phosphate, vegetable oil, carboxymethylcellulose, sodium laurylsulfate, water, ethanol, glycerin, mannitol, and syrup.

The present invention will next be described in further detail by the following examples and tests.

Example 1

Synthesis of benzyl 3-(2-pyrrolecarboxamido)propionate (Compound No. 1)

A solution of 5.34 g (48.1 mmol) of pyrrole-2-carboxylic acid and 18.59 g (52.9 mmol) of β-alanine benzyl ester tosylate in 100 ml of dimethylformamide (DMF) was cooled to 0° C., followed by the addition of a solution of 9.42 g (57.7 mmol) of diethyl cyanophosphate in 20 ml of DMF under stirring. After a solution of 11.68 g (115.4 mmol) of triethylamine in 20 ml of DMF was gradually added further dropwise, the resultant mixture was stirred for 40 hours at room temperature.

A mixed solvent (400 ml) of ethyl acetate and benzene (2:1 v/v) was added to the reaction mixture. The organic layer was washed successively with a saturated aqueous solution of sodium hydrogencarbonate, water (three times) and saturated saline, followed by drying over anhydrous sodium sulfate.

The solvent was distilled off under reduced pressure and the resultant solid was recrystallized from chloroform-isopropyl ether, whereby 11.65 g of the title compound were obtained (yield: 95%).

Appearance: Colorless prism crystals.
Melting point: 82°–83° C.

Example 2

Synthesis of ethyl 3-(N-methyl-2-pyrrolecarboxamido)-propionate (Compound No. 2)

A solution of 50.0 g (450 mmol) of pyrrole-2-carboxylic acid and 64.9 g (495 mmol) of ethyl 3-(methylamino)-propionate in 200 ml of dimethylformamide (DMF) was cooled to 0° C., followed by the addition of a solution of 80.8 g (495 mmol) of diethyl cyanophosphate in 100 ml of DMF under stirring. After a solution of 50.1 g (495 mmol) of triethylamine in 100 ml of DMF was added dropwise at the same temperature over 1 hour, the resultant mixture was stirred for 18 hours at room temperature.

To an oil obtained by concentrating the reaction mixture under reduced pressure, 1200 ml of a mixed solvent of ethyl acetate and benzene (3:1 v/v) was added. The organic layer was washed successively with a saturated aqueous solution of potassium carbonate, water, 5% hydrochloric acid solution water (twice) and saturated saline, followed by drying over anhydrous sodium sulfate. To an oil obtained by distilling off the solvent under reduced pressure, isopropyl ether (200 ml) and hexane (1000 ml) were added. After the resultant mixture was shaken, it was allowed to stand for one day.

Precipitated crystals were collected by filtration and then dried under reduced pressure, whereby 87.5 g of the title compound were obtained as colorless glossy crystalline powder (yield: 87%).

Although this compound is sufficiently pure, it can be recrystallized from isopropyl ether if necessary.

Appearance: Colorless prism crystals.
Melting point: 57°–58° C.

Example 3

The following compounds (Compound No. 3, 4, 5 and 7) were obtained by using ethyl 3-(ethylamino)propionate, ethyl 3-(propylamino)propionate, ethyl 3-(isopropylamino)propionate and ethyl 3-(benzylamino)propionate in place of ethyl 3-(methylamino)propionate in the procedure described in Example 2.

(Compound No. 3)
Ethyl 3-(N-ethyl-2-pyrrolecarboxamido)propionate
(Compound No. 4)
Ethyl 3-(N-propyl-2-pyrrolecarboxamido)propionate
(Compound No. 5)
Ethyl 3-(N-isopropyl-2-pyrrolecarboxamido)propionate
(Compound No. 7)
Ethyl 3-(N-benzyl-2-pyrrolecarboxamido)propionate

Example 4

Synthesis of ethyl 3-(N-methyl-2-pyrrolecarboxamido)-propionate (Compound No. 2) (alternative process)

To a solution of 5.56 g (50 mmol) of pyrrole-2-carboxylic acid and one droplet of DMF in 50 ml of tetrahydrofuran (THF) were added dropwise 6.54 ml (75 mmol) of oxalyl chloride under stirring and ice cooling at 0° C., and the resultant mixture was stirred for 2 hours at room temperature. The reaction mixture was concentrated under reduced pressure so that crystals of the acid chloride were obtained.

A solution of the above-obtained acid chloride in 40 ml of benzene was slowly added dropwise under cooling and stirring to a solution of 6.56 g (50 mmol) of ethyl 3-(methylamino)propionate and 4.85 ml (60 mmol) of pyridine in 20 ml of benzene. The resulting mixture was stirred for 30 minutes at the same temperature and for additional 18 hours at room temperature. The reaction mixture was filtered and the filtrate was concentrated under reduced pressure. Upon recrystallization of the resultant crystals from isopropyl ether, 10.2 g of the title compound were obtained (yield: 91%).

Example 5

Synthesis of ethyl 3-(N-butyl-2-pyrrolecarboxamido)-propionate (Compound No. 6)

The title compound was obtained by using ethyl 3-(butylamino)propionate in place of ethyl 3-(methylamino)propionate in the procedure described in Example 4.

Example 6

Synthesis of 3-(N-methyl-2-pyrrolecarboxamido)propionic acid (Compound 9)

A mixture of 37.00 g (165 mmol) of Compound No. 2 obtained in Example 2, 413 ml (826 mmol) of 2N aqueous solution of sodium hydroxide and 20 ml of ethanol was stirred for 4 hours at room temperature. The reaction mixture was cooled, and 80 ml of concentrated hydrochloric acid were added under stirring, followed by further stirring. Precipitated crystals were then collected by filtration.

The filtrate was saturated with sodium chloride, followed by extraction with ethyl acetate. The extract was dried over anhydrous sodium sulfate and the solvent was distilled off under reduced pressure, whereby crystals were obtained.

Both crystals were combined and recrystallized from ethyl acetate, whereby 27.69 g of the title compound were obtained (yield: 86%).

Appearance: Colorless prism crystals.
Melting point: 125°–127° C.

Example 7

The following compounds (Compound Nos. 10, 11, 12, 13 and 14) were obtained by using Compound Nos. 3, 4, 5, 6 and 7 in place of Compound No. 2 in the procedure described in Example 6.
(Compound No. 10)
3-(N-Ethyl-2-pyrrolecarboxamido)propionic acid
(Compound No. 11)
3-(N-Propyl-2-pyrrolecarboxamido)propionic acid
(Compound No. 12)
3-(N-Isopropyl-2-pyrrolecarboxamido)propionic acid
(Compound No. 13)
3-(N-Butyl-2-pyrrolecarboxamido)propionic acid
(Compound No. 14)
3-(N-Benzyl-2-pyrrolecarboxamido)propionic acid

Example 8

Synthesis of 3-(2-pyrrolecarboxamido)propionic acid (Compound No. 8)

Hydrogen was blown at atmospheric pressure into a suspension of 10.00 g (39.3 mmol) of Compound No. 1 obtained in Example 1 and 2.00 g of 5% palladium-carbon in 300 ml of THF while the suspension was stirred. After the full consumption of the starting material was confirmed by thin layer chromatography on silica gel (about 1 hour), the reaction mixture was filtered and an insoluble matter was washed with THF.

The filtrate and the washing were combined, and the solvent was distilled off under reduced pressure. The resulting solid was recrystallized from acetonitrile, whereby 5.61 g of the title compound were obtained (yield: 78%).

Appearance: Colorless prism crystals.
Melting point: 148°–150° C.

Example 9

Synthesis of 7-methyl-6,7-dihydropyrrolo[2,3-c]azepine-4,8(1H,5H)-dione (Compound No. 16)

A mixture of 7.00 g of Compound No. 9 obtained in Example 6 and 250 g of polyphosphoric acid (about 80%) was vigorously stirred for 30 minutes by a mechanical stirrer over an oil bath maintained at 100° C.

The reaction mixture was poured into 700 ml of ice water, followed by extraction with chloroform. The organic layer was washed with saturated saline (twice) and then dried over anhydrous sodium sulfate.

The solvent was distilled off under reduced pressure, whereby 5.58 g of the title compound were obtained as pale brown crystals (yield: 88%).

Although this compound is sufficiently pure, it can be recrystallized from chloroform-isopropyl ether if necessary.

Appearance: Colorless needle crystals.
Melting point: 175°–177° C.

Example 10

The following compounds (Compound Nos. 15, 17, 18, 19 and 21) were obtained by using Compound Nos. 8, 10, 11, 12 and 14 in place of Compound No. 9 in the procedure of Example 9.
(Compound No. 15)
6,7-Dihydropyrrolo[2,3-c]azepine-4,8(1H,5H)-dione
(Compound No. 17)
7-Ethyl-6,7-dihydropyrrolo[2,3-c]azepine-4,8-(1H,5H)-dione
(Compound No. 18)
7-Propyl-6,7-dihydropyrrolo[2,3-c]azepine-4,8-(1H,5H)-dione
(Compound No. 19)
7-Isopropyl-6,7-dihydropyrrolo[2,3-c]azepine-4,8 (1H,5H) -dione
(Compound No. 21)
7-Benzyl-6,7-dihydropyrrolo[2,3-c]azepine-4,8-(1H,5H)-dione

Example 11

Synthesis of 7-butyl-6,7-dihydropyrrolo[2,3-c]azepine-4,8(1H,5H)-dione (Compound No. 20)

A mixture of 10.0 g (42.0 mmol) of Compound No. 13 and 200 g of polyphosphoric acid (about 80%) was vigorously stirred for 30 minutes by a mechanical stirrer over an oil bath maintained at 80° C. After 3.02 g of diphosphorus pentaoxide were added and the resultant mixture was stirred for 1 minute, 10.0 g (42.0 mm) of Compound No. 13 were added and the mixture thus formed was vigorously stirred for 30 minutes at the same temperature.

The reaction mixture was poured into 750 ml of ice water, followed by extraction with chloroform. The organic layer was washed with saturated saline (twice) and then dried over anhydrous sodium sulfate.

The solvent was distilled off under reduced pressure, whereby 16.73 g of the title compound were obtained as pale brown crystals (yield: 91%). Appearance: Pale brown needle crystals.

Melting point: 115°–118° C.

Example 12

Synthesis of 7-methyl-6,7-dihydropyrrolo[2,3-c]azepine-4,8-(1H,5H)-dione (Compound No. 16) (alternative process)

A mixture of 329 mg (2 mmol) of Compound No. 9 obtained in Example 6 and 15 ml of methanesulfonic acid was stirred for 40 minutes at 100° C. The reaction mixture was allowed to cool down and then poured into 200 ml of ice water. The resultant mixture was adjusted to about pH 5 with potassium carbonate and then saturated with sodium chloride. The aqueous layer was extracted with chloroform. The extract was washed with saturated saline and then dried over anhydrous sodium sulfate.

The solvent was distilled off under reduced pressure, whereby 337 mg of the title compound were obtained as a pale brown solid.

Although this compound is sufficiently pure, it can be recrystallized from chloroform-isopropyl ether if necessary.

Example 13

Synthesis of 7-ethyl-6,7-dihydropyrrolo[2,3-c]azepine-4,8(1H,5H)-dione (Compound No. 17) (alternative process)

To a solution of 2.104 g (10 mmol) of Compound No. 10 in 30 ml of THF, 1.523 g (12 mmol) of oxalyl chloride and 1 droplet of DMF were added at room temperature under stirring. The resultant mixture was stirred for 3 hours at the same temperature, and the solvent was distilled off under reduced pressure.

The residue was then dissolved in 100 ml of 1,2-dichloroethane, followed by the addition of 4.00 g (30 mmol) of ground aluminum chloride. After the reaction mixture was heated at 50°–60° C. for 2 hours, the reaction mixture was stirred for 20 hours at room temperature. The reaction mixture was poured into 300 ml of ice water. The mixture thus prepared was allowed to separate into water and organic layers. The aqueous layer was extracted with chloroform. The extract and the organic layer were combined together, washed with saturated saline, and dried over anhydrous sodium sulfate. The solvent was then distilled off under reduced pressure.

The resultant solid was purified by chromatography on a silica gel column using as silica gel "Art. 9385" (product of Merck & Co.; the same silica gel was also used in the subsequent examples) (eluent: 3:2 mixed solvent of ethyl acetate and hexane), whereby 1.540 g of the title compound was obtained as a colorless solid (yield: 80%).

Although this compound is sufficiently pure, it can be recrystallized from isopropanol if necessary.

Appearance: Colorless needle crystals.
Melting point: 131°–133° C.

Example 14

Synthesis of 1-(4-chlorobutyl)-7-methyl-6,7-dihydropyrrolo[2,3-c]azepine-4,8(1H,5H)-dione (Compound 23)

A suspension of 2.67 g (15 mmol) of Compound No. 16 obtained in Example 9, 7.62 g (60 mmol) of 1,4-dichlorobutane and 8.29 g (60 mmol) of potassium carbonate in 150 ml of DMF was stirred at 80° C. for 5 hours.

The reaction mixture was poured into 200 ml of 5% hydrochloric acid, followed by the addition of 500 ml of a mixed solvent of ethyl acetate and benzene (2:1, v/v). The resultant mixture was allowed to separate into an organic layer and a water layer. The organic layer was washed with water (three times) and saturated saline, and was then dried over anhydrous sodium sulfate.

The solvent was distilled off under reduced pressure. The resultant oil was purified by chromatography on a silica gel column (eluent: 1:1 mixed solvent of ethyl acetate and hexane), whereby 3.907 g of the title compound were obtained as colorless crystals (yield: 97%).

Although this compound is sufficiently pure, it can be recrystallized from ethyl acetate-hexane if necessary.

Appearance: Colorless prism crystals.
Melting point: 59.0°–60.5° C.

Example 15

Compound Nos. 22, 30, 31, 32 and 34 were obtained by using Compound Nos. 15, 17, 18, 19 and 21 in place of Compound No. 16 in the procedure of Example 14.

Compound Nos. 24, 25, 26, 27, 28 and 29 were obtained by using Compound No. 16 and 1,4-dibromobutane, (Z)-1,4-dichloro-2-butene, (E)-1,4-dichloro-2-butene, 1,4-dichloro-2-butyne, 1,3-dichloropropane and 1,5-dichloropentane in place of 1,4-dichlorobutane.

Compound No. 35 was obtained from the combination of Compound 21 and 1,4-dibromobutane.

(Compound No. 22)
1-(4-Chlorobutyl)-6,7-dihydropyrrolo[2,3-c]azepine-4,8(1H,5H)-dione (Compound No. 30)
1-(4-Chlorobutyl)-7-ethyl-6,7-dihydropyrrolo[2,3-c]azepine-4,8(1H,5H)-dione (Compound No. 31)
1-(4-Chlorobutyl)-7-propyl-6,7-dihydropyrrolo[2,3-c]azepine-4,8(1H,5H)-dione (Compound No. 32)
1-(4-Chlorobutyl)-7-isopropyl-6,7-dihydropyrrolo[2,3-c]azepine-4,8(1H,5H)-dione (Compound No. 34)
7-Benzyl-1-(4-chlorobutyl)-6,7-dihydropyrrolo[2,3-c]azepine-4,8(1H,5H)-dione (Compound No. 24)
1-(4-Bromobutyl)-7-methyl-6,7-dihydropyrrolo[2,3-c]azepine-4,8(1H,5H)-dione (Compound No. 25)
1-(4-Chloro-(Z)-2-butenyl)-7-methyl-6,7-dihydropyrrolo[2,3-c]azepine-4,8(1H,5H)-dione (Compound No. 26)
1-(4-Chloro-(E)-2-butenyl)-7-methyl-6,7-dihydropyrrolo[2,3-c]azepine-4,8(1H,5H)-dione (Compound No. 27)
1-(4-Chloro-2-butynyl)-7-methyl-6,7-dihydropyrrolo[2,3-c]azepine-4,8(1H,5H)-dione (Compound No. 28)

1-(3-Chloropropyl)-7-methyl-6,7-dihydropyrrolo[2,3-c]azepine-4,8(1H,5H)-dione
(Compound No. 29)
1-(5-Chloropentyl)-7-methyl-6,7-dihydropyrrolo[2,3-c]azepine-4,8(1H,5H)-dione
(Compound No. 35)
7-Benzyl-1-(4-bromobutyl)-6,7-dihydropyrrolo[2,3-c]azepine-4,8(1H,5H)-dione

Example 16

Synthesis of 7-butyl-1-(4-chlorobutyl)-6,7-dihydropyrrolo[2,3-c]azepine-4,8(1H,5H)-dione (Compound No. 33)

A suspension of 16.47 g (74.48 mmol) of Compound No. 20 obtained in Example 11, 38.46 g (224 mmol) of 1-bromo-4-chlorobutane and 31.00 g (224 mmol) of potassium carbonate in 200 ml of acetone was stirred for 20 hours.

The reaction mixture was filtered to remove any insoluble matter and the solvent and excess 1-bromo-4-cholorobutane were distilled off under reduced pressure, whereby 22.0 g of the title compound were obtained (yield: 98%).

Appearance: Colorless oil.

Example 17

Synthesis of 1-(4-chlorobutyl)-4-hydroxyimino-7-methyl-6,7-dihydropyrrolo[2,3-c]azepin-8(1H,5H)-one (Compound No. 38)

A solution of 4.031 g (15 mmol) of Compound No. 23 obtained in Example 14 and 5.212 g (75 mmol) of hydroxylamine hydrochloride in 90 ml of pyridine was stirred for 18 hours at room temperature.

After the reaction mixture was concentrated under reduced pressure, toluene was added, followed by concentration again under reduced pressure. The residue was added with 200 ml of a 10% aqueous solution of citric acid and then extracted with chloroform. The extract was washed with saturated saline and then dried over anhydrous sodium sulfate.

The solvent was distilled off under reduced pressure and the resultant oil was purified by chromatography on a silica gel column (eluent: 7.5% methanol-chloroform), whereby 3.84 g of a colorless oil were obtained (yield: 90%). The oil was crystallized when treated with isopropyl ether.

Although this compound is sufficiently pure, it can be recrystallized from ethyl acetate if necessary. Appearance: Colorless needle crystals.

Melting point: 113.0°-114.0° C.

Example 18

Compound Nos. 36, 41, 37, 42, 43, 44, 45 and 47 were obtained by using Compound Nos. 22, 24, 28, 29, 30, 31, 32 and 34 in place of Compound No. 23 in the procedure of Example 17.
(Compound No. 36)
1-(4-Chlorobutyl)-4-hydroxyimino-6,7-dihydropyrrolo[2,3-c]azepin-8(1H,5H)-one
(Compound No. 37)
1-(3-Chloropropyl)-4-hydroxyimino-7-methyl-6,7-dihydropyrrolo[2,3-c]azepin-8(1H,5H)-one
(Compound No. 41)
1-(4-Bromobutyl)-4-hydroxyimino-7-methyl-6,7-dihydropyrrolo[2,3-c]azepin-8(1H,5H)-one
(Compound No. 42)
1-(5-Chloropentyl)-4-hydroxyimino-7-methyl-6,7-dihydropyrrolo[2,3-c]azepin-8(1H,5H)-one
(Compound No. 43)
1-(4-Chlorobutyl)-7-ethyl-4-hydroxyimino-6,7-dihydropyrrolo[2,3-c]azepin-8(1H,5H)-one
(Compound No. 44)
1-(4-Chlorobutyl)-4-hydroxyimino-7-propyl-6,7-dihydropyrrolo[2,3-c]azepin-8(1H,5H)-one
(Compound No. 45)
1-(4-Chlorobutyl)-4-hydroxyimino-7-isopropyl-6,7-dihydropyrrolo[2,3-c]azepin-8(1H,5H)-one
(Compound No. 47)
7-Benzyl-1-(4-chlorobutyl)-4-hydroxyimino-6,7-dihydropyrrolo[2,3-c]azepin-8(1H,5H)-one

Example 19

Synthesis of 7-butyl-1-(4-chlorobutyl)-4-hydroxyimino-6,7-dihydropyrrolo[2,3-c]azepin-8(1H,5H)-one (Compound No. 46)

A solution of 21.0 g (67.6 mmol) of Compound No. 33 obtained in Example 16, 14.1 g (203 mmol) of hydroxylamine hydrochloride and 16.6 g (203 mmol) of anhydrous sodium acetate in 150 ml of methanol was stirred for 24 hours at room temperature.

The reaction mixture was concentrated under reduced pressure, added with 500 ml of chloroform, washed with a 5% aqueous solution of hydrochloric acid, a half-saturated aqueous solution of potassium carbonate and saturated saline, and then dried over anhydrous sodium sulfate.

The solvent was distilled off under reduced pressure, whereby 19.0 g of the title compound were obtained as pale brown crystals (yield: 86%).

Although this compound is sufficiently pure, it can be recrystallized from ethanol if necessary. Appearance: Pale brown needle crystals.

Melting point: 133°-136° C.

Example 20

Synthesis of 1-(4-chlorobutyl)-4-methoxyimino-7-methyl-6,7-dihydropyrrolo[2,3-c]azepin-8(1H,5H)-one (Compound No. 39)

A solution of 210 mg (0.74 mmol) of Compound No. 23 obtained in Example 14 and 68 mg (0.82 mmol) of O-methylhydroxylamine hydrochloride in 10 ml of pyridine was stirred for 4 hours at 80° C.

The reaction mixture was concentrated under reduced pressure. The residue was added with 20 ml of a half-saturated aqueous solution of potassium carbonate and was then extracted with chloroform. The extract was washed with saturated saline, followed by drying over anhydrous sodium sulfate.

The solvent was distilled off under reduced pressure and the resultant oil was purified by chromatography on a silica gel column (eluent: 3:7 mixed solvent of ethyl acetate and hexane), whereby 104 mg of the title compound were obtained (yield: 47%).

Appearance: Colorless oil.

Example 21

Synthesis of 4-benzyloxyimino-1-(4-chlorobutyl)-7-methyl-6,7-dihydropyrrolo[2,3-c]azepin-8(1H,5H)-one (Compound No. 40)

A suspension of 13.44 g (50 mmol) of Compound 23 obtained in Example 14, 8.20 g (100 mmol) of sodium acetate and 15.96 g (100 mmol) of O-benzylhydroxylamine hydrochloride in 250 ml of methanol was stirred for 4 hours at room temperature.

The solvent was distilled off under reduced pressure, followed by the addition of 600 ml of ethyl acetate to the residue. The organic layer was washed with 1N-HCl (three times), H₂O and saturated saline and was then dried over anhydrous sodium sulfate. The solvent was distilled off under reduced pressure and the resultant pale yellow oil was purified by chromatography on a silica gel column (eluent: 2:3 mixed solvent of ethyl acetate and hexane), whereby 16.20 g of the title compound were obtained as a colorless oil. The oil was crystallized when treated in isopropyl ether (yield: 87%).

Although this compound is sufficiently pure, it can be recrystallized from isopropyl ether if necessary.

Appearance: colorless prism crystals.
Melting point: 62°-64° C.

Example 22

Synthesis of 1-[4-[4-(4-fluorobenzoyl)piperidin-1-yl]butyl]-7-methyl-6,7-dihydropyrrolo[2,3-c]azepine-4,8(1H,5H)-dione (Compound No. 60)

A suspension of 1.57 g (5 mmol) of Compound No. 24 obtained in Example 15, 2.07 g (10 mmol) of 4-(4-fluorobenzoyl)piperidine and 1.38 g (10 mmol) of potassium carbonate in 60 ml of DMF was stirred for 20 hours at 80° C. After allowed to cool down, the reaction mixture was filtered. A solid matter was washed with ethyl acetate. The filtrate and the washing were combined together, followed by concentration under reduced pressure. The residue was added with 400 ml of a 3:1 (v/v) mixed solvent of ethyl acetate and benzene. The organic layer was washed with water (three times) and saturated saline, and then dried over anhydrous sodium sulfate.

The solvent was distilled off under reduced pressure and the resultant brown oil was purified by chromatography on a silica gel column (eluent: 5% methanol-chloroform), whereby 1.89 g of the title compound were obtained (yield: 86%).

Appearance: Yellow oil.

Example 23

Compound Nos. 67, 68 and 69 were obtained by using Compound Nos. 25, 26 and 27 in place of Compound No. 24 in the procedure described in Example 22.

Further, Compound Nos. 52, 53, 54, 55, 72 and 78 were obtained from Compound No. 24 and 4-benzylpiperidine, 4-[bis(4-fluorophenyl)methylene]piperidine, α,α-bis(4-fluorophenyl)-4-piperidinemethanol, 4-(diphenylmethoxy)piperidine, 4-(4-methoxybenzoyl)-piperidine and 3-benzoylpyrrolidine, respectively.

Further, Compound No. 48 was obtained from Compound No. 35 and 4-phenylpiperidine.
(Compound No. 67)
1-[4-[4-(4-Fluorobenzoyl)piperidin-1-yl]-(Z)-2-butenyl]-7-methyl-6,7-dihydropyrrolo[2,3-c]azepine-4,8(1H,5H)-dione
(Compound No. 68)
1-[4-[4-(4-Fluorobenzoyl)piperidin-1-yl]-(E)-2-butenyl]-7-methyl-6,7-dihydropyrrolo[2,3-c]azepine-4,8(1H,5H)-dione
(Compound No. 69)
1-[4-[4-(4-Fluorobenzoyl)piperidin-1-yl]-2-butynyl]-7-methyl-6,7-dihydropyrrolo[2,3-c]azepine-4,8(1H,5H)-dione
(Compound No. 52)
1-[4-(4-Benzylpiperidin-1-yl)butyl]-7-methyl-6,7-dihydropyrrolo[2,3-c]azepine-4,8(1H,5H)-dione
(Compound No. 53)
1-[4-[4-[Bis(4-fluorophenyl)methylene]piperidin-1-yl]butyl]-7-methyl-6,7-dihydropyrrolo[2,3-c]azepine-4,8(1H,5H)-dione
(Compound No. 54)
1-[4-[4-[Bis(4-fluorophenyl)hydroxymethyl]piperidin-1-yl]butyl]-7-methyl-6,7-dihydropyrrolo[2,3-c]azepine-4,8(1H,5H)-dione
(Compound No. 55)
1-[4-[4-(Diphenylmethoxy)piperidin-1-yl]butyl]-7-methyl-6,7-dihydropyrrolo[2,3-c]azepine-4,8(1H,5H)-dione
(Compound No. 72)
1-[4-[4-(4-Methoxybenzoyl)piperidin-1-yl]butyl]-7-methyl-6,7-dihydropyrrolo[2,3-c]azepine-4,8(1H,5H)-dione
(Compound No. 78)
1-[4-(3-Benzoylpyrrolidin-1-yl)butyl]-7-methyl-6,7-dihydropyrrolo[2,3-c]azepine-4,8(1H,5H)-dione
(Compound No. 48)
7-Benzyl-1-[4-(4-phenylpiperidin-1-yl)butyl]-6,7-dihydropyrrolo[2,3-c]azepine-4,8(1H,5H)-dione

Example 24

Synthesis of 1-[4-[4-(4-fluorobenzoyl)piperidin-1-yl]butyl]-4-hydroxyimino-7-methyl-6,7-dihydropyrrolo[2,3-c]azepine-8-(1H,5H)-one (Compound No. 61)

A suspension of 2.838 g (10 mmol) of Compound No. 38 obtained in Example 17, 4.874 g (20 mmol) of 4-(4-fluorobenzoyl)piperidine hydrochloride and 5.528 g (40 mmol) of potassium carbonate in 150 ml of DMF was stirred for 14 hours at 80° C. The reaction mixture was filtered, a solid matter was washed with chloroform, and the filtrate and the washing were combined together, followed by concentration under reduced pressure.

The residue was added with 600 ml of a 2:1 (v/v) mixed solvent of ethyl acetate and benzene. The organic layer was washed with a half-saturated aqueous solution of potassium carbonate, water (three times) and saturated saline, and was then dried over anhydrous sodium sulfate.

The solvent was distilled off under reduced pressure and the resultant brown oil was purified by chromatography on a silica gel column (eluent: 10% methanol-chloroform), whereby 3.28 g of the title compound was obtained as a colorless oil. When treated in isopropyl ether, the oil was crystallized (yield: 72%).

Although the compound is sufficiently pure, it can be recrystallized from isopropanol if necessary.

Appearance: Colorless needle crystals.
Melting point: 166°-168° C.

Example 25

Synthesis of 1-[4-[4-(4-fluorobenzoyl)piperidin-1-yl]butyl]-4-hydroxyimino-7-methyl-6,7-dihydropyrrolo[2,3-c]azepin-8(1H,5H)-one p-toluenesulfonate (Compound No. 62)

A mixture of 5.0 g (11.0 mmol) of Compound 61 obtained in Example 24 and 2.1 g (11.0 mmol) of p-toluenesulfonic acid monohydrate was heated in 120 ml of ethanol, so that the latter compounds were dissolved. The resultant mixture was allowed to cool down, whereby 6.5 g of the title compound were obtained as colorless crystals (yield: 92%).

Appearance: Colorless needle crystals.
Melting point: 197°-198° C.

Example 26

Compound Nos. 58, 59 and 63 were obtained by using Compound Nos. 28, 37 and 29 in place of Compound No. 38 in the procedure described in Example 24.

Compound No. 73 was also obtained by using 4-(4-chlorobenzoyl)piperidine hydrochloride in place of 4-(4-fluorobenzoyl)piperidine hydrochloride.

Further, Compound No. 66 was obtained from Compound No. 47 and 4-(4-fluorobenzoyl)piperidine, and Compound Nos. 70 and 71 from Compound Nos. 24 and 41 and 4-benzoylpiperidine, respectively.

(Compound No. 58)
1-[3-[4-(4-Fluorobenzoyl)piperidin-1-yl]propyl]-7-methyl-6,7-dihydropyrrolo[2,3-c]azepine-4,8(1H,5H)-dione (Compound No. 59)
1-[3-[4-(4-Fluorobenzoyl)piperidin-1-yl]propyl]-4-hydroxyimino-7-methyl-6,7-dihydropyrrolo[2,3-c]azepin-8(1H,5H)-one (Compound No. 63)
1-[5-[4-(4-Fluorobenzoyl)piperidin-1-yl]pentyl]-7-methyl-6,7-dihydropyrrolo[2,3-c]azepine-4,8(1H,5H)-dione (Compound No. 73)
1-[4-[4-(4-Chlorobenzoyl)piperidin-1-yl]butyl]-4-hydroxyimino-7-methyl-6,7-dihydropyrrolo[2,3-c]azepin-8(1H,5H)-one (Compound No. 66)
7-Benzyl-1-[4-[4-(4-fluorobenzoyl)piperidin-1-yl]butyl]-4-hydroxyimino-6,7-dihydropyrrolo[2,3-c]azepin-8(1H,5H)-one (Compound No. 70)
1-[4-(4-Benzoylpiperidin-1-yl)butyl]-7-methyl-6,7-dihydropyrrolo[2,3-c]azepine-4,8(1H,5H)-dione (Compound No. 71)
1-[4-(4-Benzoylpiperidin-1-yl)butyl]-4-hydroxyimino-7-methyl-6,7-dihydropyrrolo[2,3-c]azepin-8(1H,5H)-one

Example 27

Synthesis of 1-[4-[4-(4-fluorophenylsulfonyl)piperidin-1-yl]butyl]-4-hydroxyimino-7-methyl-6,7-dihydropyrrolo[2,3-c]azepin-8(1H,5H)-one (Compound No. 87)

A suspension of 150 mg (0.53 mmol) of Compound No. 38 obtained by the procedure of Example 17, 177 mg (0.63 mmol) of 4-(4-fluorophenylsulfonyl)piperidine hydrochloride, 0.22 ml (1.59 mmol) of triethylamine and 149 mg (1.06 mmol) of sodium iodide in 3 ml of DMF was heated for 25 hours at 80° C. under stirring.

The reaction mixture was then post-treated and purified as in Example 24, whereby 230 mg of the title compound were obtained as colorless crystals (yield: 89%). Although the compound is sufficiently pure, it can be recrystallized from methanol-ethanol if necessary.

Appearance: Colorless needle crystals.
Melting point: 190°-192° C.

Example 28

Following the procedure described in Example 27, the following compounds were prepared from the corresponding various combinations of starting materials. Compound Nos. 85 and 86 were obtained from Compound No. 38 and 4-[(4-fluorophenyl)thio]piperidine hydrochloride and 4-[(4-fluorophenyl)sulfinyl]piperidine hydrochloride, respectively.

Further, Compound Nos. 80, 94 and 88 were obtained from 4-(4-fluorobenzoyl)piperidine hydrochloride and Compound Nos. 39, 31 and 33, respectively.

(Compound No. 85)
1-[4-[4-[(4-Fluorophenyl)thio]piperidin-1-yl]butyl]-4-hydroxyimino-7-methyl-6,7-dihydropyrrolo[2,3-c]azepin-8(1H,5H)-one (Compound No. 86)
1-[4-[4-[(4-Fluorophenyl)sulfinyl]piperidin-1-yl]butyl]-4-hydroxyimino-7-methyl-6,7-dihydropyrrolo[2,3-c]azepin-8(1H,5H)-one (Compound No. 80)
1-[4-[4-[(4-Fluorobenzoyl)piperidin-1-yl]butyl]-4-methoxyimino-7-methyl-6,7-dihydropyrrolo[2,3-c]azepin-8(1H,5H)-one (Compound No. 94)
1-[4-[4(4-Fluorobenzoyl)piperidin-1-yl]butyl]-7-propyl-6,7-dihydropyrrolo[2,3-c]azepine-4,8(1H,5H)-dione (Compound No. 88)
7-Butyl-1-[4-[4-(4-fluorobenzoyl)piperidin-1-yl]butyl]-6,7-dihydropyrrolo[2,3-c]azepine-4,8(1H,5H)-dione

Example 29

Synthesis of 7-ethyl-1-[4-[4-(4-fluorobenzoyl)piperidin-1-yl]butyl]-4-hydroxyimino-6,7-dihydropyrrolo[2,3-c]azepin-8-(1H,5H)-one (Compound No. 65)

A suspension of 5.062 g (17 mmol) of Compound No. 43, 4.228 g (20.4 mmol) of 4-(4-fluorobenzoyl)piperidine, 3.440 g (34 mmol) of triethylamine and 5.069 g (34 mmol) of sodium iodide in 200 ml of DMF stirred for 20 hours at 80° C.

The reaction mixture was then post-treated and purified as in Example 24. Recrystallization from ethanol gave 5.47 g of the title compound (yield: 69%).

Appearance: Colorless needle crystals.
Melting point: 158°-160° C.

Example 30

Following the procedure described in Example 29, the following compounds were prepared from the corresponding various combinations of starting materials.

Compound Nos. 74, 75, 76, 81, 82, 83 and 89 were obtained from 4-(4-fluorobenzoyl)piperidine and Compound Nos. 36, 44, 45, 22, 30, 34 and 46, respectively.

Further, Compound Nos. 77 and 84 were obtained from Compound No. 38 and 3-(4-fluorobenzoyl)piperidine and 4-(4-fluorophenoxy)piperidine, respectively.

(Compound No. 74)
1-[4-[4-(4-Fluorobenzoyl)piperidin-1-yl]butyl]-4-hydroxyimino-6,7-dihydropyrrolo[2,3-c]azepin-8(1H,5H)-one (Compound No. 75)
1-[4-[4-(4-Fluorobenzoyl)piperidin-1-yl]butyl]-4-hydroxyimino-7-propyl-6,7-dihydropyrrolo[2,3-c]azepin-8(1H,5H)-one (Compound No. 76)
1-[4-[4-(4-Fluorobenzoyl)piperidin-1-yl]butyl]-4-hydroxyimino-7-isopropyl-6,7-dihydropyrrolo[2,3-c]azepin-8(1H,5H)-one (Compound No. 81)
1-[4-[4-(4-Fluorobenzoyl)piperidin-1-yl]butyl]-6,7-dihydropyrrolo[2,3-c]azepine-4,8(1H,5H)-dione (Compound No. 82)
7-Ethyl-1-[4-[4-(4-fluorobenzoyl)piperidin-1-yl]butyl]-6,7-dihydropyrrolo[2,3-c]azepine-4,8(1H,5H)-dione (Compound No. 83)
7-Benzyl-1-[4-[4-(4-fluorobenzoyl)piperidin-1-yl]butyl]-6,7-dihydropyrrolo[2,3-c]azepine-4,8(1H,5H)-dione (Compound No. 89)
7-Butyl-1-[4-[4-(4-fluorobenzoyl)piperidin-1-yl]butyl]-4-hydroxyimino-6,7-dihydropyrrolo[2,3-c]azepin-8(1H,5H)-one
(Compound No. 77)
1-[4-[3-(4-Fluorobenzoyl)piperidin-1-yl]butyl]-4-hydroxyimino-7-methyl -6,7-dihydropyrrolo[2,3-c]azepin-8(1H,5H)-one
(Compound No. 84)
1-[4-[4-(4-Fluorophenoxy)piperidin-1-yl]butyl]-4-hydroxyimino-7-methyl-6,7-dihydropyrrolo[2,3-c]azepin-8(1H,5H)-one

Example 31

Synthesis of 4-benzyloxyimino-1-[4-[4-(4-fluorobenzoyl)piperidin-1-yl]butyl]-7-methyl-6,7-dihydropyrrolo[2,3-c]azepin-8-(1H,5H)-one (Compound No. 90)

A suspension of 7.48 g (20 mmol) of Compound No. 40 obtained in Example 21, 5.85 g (24 mmol) of 4-(4-fluorobenzoyl)piperidine hydrochloride, 6.48 g (64 mmol) of triethylamine and 6.00 g (40 mmol) of sodium iodide in 300 ml of acetonitrile was refluxed for 24 hours. The reaction mixture was concentrated under reduced pressure. The residue was added with 300 ml of a half-saturated aqueous solution of potassium carbonate and then extracted with dichloromethane (300 ml × twice).

The dichloromethane layer was washed with saturated saline and then dried over anhydrous sodium sulfate. The solvent was distilled off under reduced pressure and the resulting brown oil was purified by chromatography on a silica gel column (eluent: 5% methanol-chloroform), whereby 8.51 g of the title compound were obtained (yield: 78%).

Appearance: Yellow oil.

Example 32

Synthesis of 1-[4-[4-[2-(4-fluorophenyl)-1,3-dioxolanyl]-piperidin-1-yl]butyl]-4-hydroxyimino-7-methyl-6,7-dihydropyrrolo[2,3-c]azepin-8-(1H,5H)-one (Compound No. 93)

A suspension of 2.838 g (10 mmol) of Compound No. 38 obtained in Example 17, 3.016 g (12 mmol) of 4-(4-fluorobenzoyl)piperidine ethyleneacetal, 2.024 g (20 mmol) of triethylamine and 2.998 g (20 mmol) of sodium iodide in 500 ml of acetonitrile was refluxed for 24 hours.

The reaction mixture was concentrated under reduced pressure. The residue was added with 300 ml of chloroform, washed with water and saturated saline, and then dried over anhydrous sodium sulfate. The solvent was distilled off under reduced pressure and the resulting yellow oil was purified by chromatography on a silica gel column (eluent: 10% methanol-chloroform), whereby 4.375 g of the title compound were obtained as a solid yellow solid (yield: 88%).

Although the compound is sufficiently pure, it can be recrystallized from isopropyl alcohol-isopropyl ether if necessary.

Appearance: Colorless prism crystals.
Melting point: 149.0°-150.5° C.

Example 33

Synthesis of 1-[4-(4-cyano-4-phenylpiperidin-1-yl)butyl]-7-methyl-6,7-dihydropyrrolo[2,3-c]azepine-4,8(1H,5H)-dione (Compound No. 56)

The title compound was obtained from Compound No. 23 obtained in Example 14 and 4-cyano-4-phenylpiperidine hydrochloride in accordance with the procedure of Example 29 except that triethylamine was replaced by the same mole number of potassium carbonate.

Example 34

Following the procedure described in Example 33, Compound Nos. 57 and 79 were obtained from the combinations of Compound No. 38 and 4-cyano-4-phenylpiperidine hydrochloride and 3-(4-fluorobenzoyl)pyrrolidine hydrochloride.

Further, Compound No. 64 was also obtained from the combination of Compound No. 42 and 4-(4-fluorobenzoyl)piperidine hydrochloride.
(Compound No. 57)
1-[4-(4-Cyano-4-phenylpiperidin-1-yl)butyl]-4-hydroxyimino-7-methyl-6,7-dihydropyrrolo[2,3-c]azepin-8(1H,5H)-one
(Compound No. 79)
1-[4-[3-(4-fluorobenzoyl)pyrrolidin-1-yl]butyl]-4-hydroxyimino-7-methyl-6,7-dihydropyrrolo[2,3-c]azepin-8(1H,5H)-one
(Compound No. 64)
1-[5-[4-(4-Fluorobenzoyl)piperidin-1-yl]pentyl]-4-hydroxyimino-7-methyl-6,7-dihydropyrrolo[2,3-c]azepin-8(1H,5H)-one

Example 35

Synthesis of 7-methyl-1-[4-(4-phenylpiperidin-1-yl)butyl]-6,7-dihydropyrrolo[2,3-c]azepine-4,8(1H,5H)-dione (Compound No. 49)

A suspension of 806 mg (3 mmol) of Compound No. 23 obtained in Example 14, 1.935 g (12 mmol) of 4-phenylpiperidine and 4.500 g (30 mmol) of sodium iodide in 70 ml of DMF was stirred for 5 hours at 80° C. The reaction mixture was allowed to cool down, followed by the addition of 500 ml of a 2:1 (v/v) mixed solvent of ethyl acetate and benzene. The organic layer was washed with a half-saturated aqueous solution of potassium carbonate, water (three times) and saturated saline, and was then dried over anhydrous sodium sulfate.

The solvent was distilled off under reduced pressure and the resultant oil was purified by chromatography on a silica gel column (eluent: 5% methanol-chloroform), whereby 1.106 g of the title compound were obtained as a pale yellow oil (yield: 94%).

The title compound which was in the free form was converted to its hydrochloride (Compound No. 50) by a method known per se in the art. The hydrochloride was recrystallized from isopropanol-isopropyl ether.
Appearance: Pale yellow plate crystals.
Melting point: 208°-210° C.

Example 36

Synthesis of 4-hydroxyimino-7-methyl-1-[4-(4-phenylpiperidin-1-yl)butyl]-6,7-dihydropyrrolo[2,3-c]azepin-8(1H,5H)-one (Compound No. 51)

A solution of 590 mg (1.5 mmol) of the free compound (Compound No. 49) obtained in Example 35 and 521 mg (7.5 mmol) of hydroxylamine hydrochloride in 40 ml of pyridine was stirred for 16 hours at room temperature.

After the reaction mixture was concentrated under reduced pressure, toluene was added. The resultant mixture was concentrated again under reduced pressure. The residue was added with 300 ml of a half-saturated aqueous solution of potassium carbonate and then extracted with chloroform. The extract was washed with saturated saline and then dried over anhydrous sodium sulfate. The solvent was distilled off under reduced pressure. The resultant oil was purified by chromatography on a silica gel column (eluent: 10% methanolchloroform), whereby 546 mg of colorless oil was obtained. The oil was treated in isopropyl ether so that it was crystallized. Although the compound is sufficiently pure, it can be recrystallized from isopropanol-ether if necessary.

Appearance: Colorless prism crystals.
Melting point: 164°-165° C.

Example 37

Synthesis of 4-acetoxyimino-1-[4-[4-(4-fluorobenzoyl)-piperidin-1-yl)butyl]-7-methyl-6,7-dihydropyrrolo[2,3-c]azepin-8(1H,5H)-one (Compound No. 91)

To a solution of 5.00 g (11.0 mmol) of Compound No. 61, which had been obtained in Example 24, in 50 ml of pyridine, 1.56 ml (22.0 mmol) of acetyl chloride were added. The resulting mixture was stirred for 3 hours at room temperature.

After the reaction mixture was concentrated under reduced pressure, 100 ml of water was added, followed by the extraction with 400 ml of dichloromethane. The organic layer was washed with saturated saline and then dried over anhydrous sodium sulfate. The solvent was distilled off and the resultant brown oil was purified by chromatography on a silica gel column (eluent: 3% methanol-chloroform), whereby 4.30 g of the title compound were obtained as a colorless oil (yield: 79%).

Appearance: Colorless oil.

Example 38

Synthesis of 4-benzoyloxyimino-1-[4-[4-(4-fluorobenzoylpiperidin)-1-yl]butyl]-7-methyl-6,7-dihydropyrrolo[2,3-c]azepin-8(1H,5H)-one (Compound No. 92)

To a solution of 227 mg (0.5 mmol) of Compound No. 61, which had been obtained in Example 24, and 92 mg (0.75 mmol) of benzoic acid in 10 ml of DMF, a solution of 122 mg (0.75 mmol) of diethyl cyanophosphonate in 5 ml of DMF and another solution of 152 mg (1.5 mmol) of triethylamine in 5 ml of DMF were added successively and gradually, and the resultant mixture was stirred for 16 hours at room temperature. The reaction mixture was added with 300 ml of a 3:1 (v/v) mixture of ethyl acetate and benzene, washed with a saturated aqueous solution of potassium carbonate, water (three times) and saturated saline, and then dried over anhydrous sodium sulfate.

The solvent was distilled off under reduced pressure and the resultant brown oil was purified by chromatography on a silica gel column (eluent: 5% methanol-chloroform), whereby 252 mg of the title compound were obtained (yield: 90%).

Appearance: Yellow oil.

Example 39

Synthesis of 4-benzoyloxyimino-1-[4-[4-(4-fluorobenzoylpiperidin)-1-yl]butyl]-7-methyl-6,7-dihydropyrrolo[2,3-c]azepine-8(1H,5H)-one (Compound No. 92) (Alternative process):

To a solution of 227 mg (0.5 mmol) of Compound 61, which had been obtained in Example 24, in 10 ml of pyridine, 1 ml of benzoyl chloride was slowly added dropwise under ice cooling and stirring. After the resultant mixture was stirred for 16 hours at room temperature, the reaction mixture was concentrated under reduced pressure. The residue was added with 300 ml of ethyl acetate. The organic layer was washed with a saturated aqueous solution of potassium carbonate (twice), water (twice) and saturated saline, and then dried over anhydrous sodium sulfate. The solvent was distilled off under reduced pressure and the resulting brown oil was purified by chromatography on a silica gel column (eluent: 5% methanol-chloroform), whereby 240 mg of the title compound were obtained (yield: 86%).

Example 40

Synthesis of 1-[4-[4-(4-fluorobenzoyl)piperidin-1-yl]butyl]-7-methyl-6,7-dihydropyrrolo[2,3-c]azepine-4,8(1H,5H)-dione benzylbromide (Compound No. 95)

1.5 ml of benzyl bromide was added to a solution of 31.5 mg (0.072 mmol) of Compound No. 60, obtained in Example 22, in 1 ml of acetone.

The resultant mixture was stirred for 21 hours at room temperature. Benzene and n-hexane were added in suitable amounts, followed by trituration. Crude crystals thus obtained were collected by filtration and washed with n-hexane (yield: 36 mg, 82%). They were recrystallized from acetone, whereby the title compound was obtained as colorless crystals.

Melting point: 150°-155° C.

Example 41

Compound Nos. 96 and 97 were obtained by changing benzyl bromide to methyl iodide and ethyl bromide, respectively in Example 40.
(Compound No. 96)
1-[4-[4-(4-Fluorobenzoyl)piperidin-1-yl]butyl]-7-methyl-6,7-dihydropyrrolo[2,3-c]azepine-4,8(1H,5H)-dione methyliodide.
(Compound No. 97)
1-[4-[4-(4-Fluorobenzoyl)piperidin-1-yl]butyl]-7-methyl-6,7-dihydropyrrolo[2,3-c]azepine-4,8(1H,5H)-dione ethylbromide.

Example 42

Synthesis of 4-benzoyloxyimino-1-(4-chlorobutyl)-7-methyl-6,7-dihydropyrrolo[2,3-c]azepine-8(1H,5H)-one (Compound No. 98)

A solution of 4.256 g (15 mmol) of Compound No. 38, which had been obtained in Example 17, and 2.748 g (22.5 mmol) of benzoic acid in 60 ml of DMF was cooled to 0° C., to which a solution of 3.670 g (22.5 mmol) of diethyl cyanophosphate in 20 ml of DMF and another solution of 2.277 g (22.5 mmol) of triethylamine in 20 mZ of DMF were successively and gradually added. The resultant mixture was stirred for 1 hour at the same temperature and for additional 4 hours at room temperature.

The reaction mixture was concentrated under reduced pressure and 600 ml of a 3:1 (v/v) mixed solvent of ethyl acetate and benzene were added to the residue. The organic layer was washed with a 10% aqueous solution of citric acid, water (three times) and saturated saline and was then dried over anhydrous sodium sulfate. The solvent was thereafter distilled off under reduced pressure. The resulting brown oil was purified by chromatography on a silica gel column (eluent: 1:1 mixed solvent of ethyl acetate and hexane) and then recrystallized from isopropyl ether, whereby 5.604 g of the title compound were obtained (yield: 87%)

Appearance: Colorless prism crystals.
Melting point: 123.5°-125.0° C.

Example 43

Synthesis of 4-benzoyloxyimino-1-[4-[4-(4-fluorobenzoyl)piperidine-1-yl]butyl]-7-methyl-6,7-dihydropyrrolo[2,3-c]azepin-8(1H,5H)-one (Compound No. 92)

A suspension of 3.879 g (10 mmol) of Compound No. 98 obtained in Example 42, 2.437 g (10 mmol) of 4-(4-fluorobenzoyl)piperidine hydrochloride, 3.000 g (20 mmol) of sodium iodide and 3.036 g (30 mmol) of triethylamine in 50 ml of $CH_3CN$ was refluxed for 20 hours.

The reaction mixture was concentrated under reduced pressure. The residue was added with 300 ml of a half-saturated aqueous solution of potassium carbonate, followed by the extraction with dichloromethane (200 ml×3 times). The dichloromethane layers were combined, washed with 200 ml of saturated saline, and then dried over anhydrous sodium sulfate. The solvent was distilled off under reduced pressure.

The resulting brown oil was purified by chromatography on a silica gel column (eluent: 10% methanol-chloroform), whereby 2.953 g of the title compound were obtained (yield: 53%).

Data of the compounds obtained in the above examples are summarized in Table 1.

TABLE 1

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 15 | Pale brown powder | (DMSO-d$_6$/TMS) 2.71(2H, m), 3.37(2H, m), 6.56(1H, m) 6.99(1H, m), 8.32(1H, t, J=4.6Hz), 12.16(1H, br.s) | (KBr) 3200, 1665, 1545 1480, 1420, 1400 1365, 1270, 1160 1075, 1005, 905 | 65 | NH structure |
| 16 | Colorless needle crystals 175.0–177.0° C. (chloroform-diisopropyl ether) | 2.89(2H, m), 3.27(3H, s), 3.73(2H, m) 6.77(1H, t, J=2.6Hz), 6.94(1H, t, J=2.6Hz), 10.84(1H, br.) | 3425, 2450, 1665 1620, 1480, 1440 1365, 1145, 1080 945 | 88 | NCH$_3$ structure |
| 17 | Colorless needle crystals 131.0–133.0° C. (isopropanol) | 1.27(3H, t, J=7.3Hz), 2.88(2H, m) 3.60–3.82(4H, m), 6.77(1H, t, J=2.6Hz), 6.94(1H, t, J=2.6Hz), 11.0(1H, br.) | 3425, 2960, 1665 1620, 1485, 1370 1300, 1145, 1110 1070 | 80 | NC$_2$H$_5$ structure |
| 18 | Colorless needle crystals 144.0–148.0° C. (ethyl acetate) | 0.99(3H, t, J=7.5Hz), 1.68(2H, m) 2.87(2H, m), 3.61(2H, t, J=7.2Hz), 3.70(2H, m), 6.78(1H, t, J=2.6Hz), 6.94(1H, t, J=2.6Hz), 10.64(1H, br.) | 3430, 2950, 1670 1620, 1480, 1370 1150, 1120, 1070 890 | 79 | NC$_3$H$_7$ structure |
| 19 | Colorless needle crystals 155.0–158.0° C. (ethyl acetate) | 1.24(6H, d, J=6.6Hz), 2.82(2H, m) 3.58(2H, m), 5.05(1H, m), 6.77(1H, m), 6.94(1H, t, J=2.7Hz), 10.42(1H, br.) | 3430, 2970, 1665 1615, 1480, 1360 1140, 1065, 885 | 89 | N—C$_3$H$_7^i$ structure |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 20 | Pale brown needle crystals 115.0–118.0° C. | 0.97(3H, t, J=7.3Hz), 1.41(2H, m) 1.64(2H, m), 2.86(2H, m) 3.64(2H, t, J=7.3Hz), 3.69(2H, m) 6.78(1H, m), 6.93(1H, m) 10.42(1H, br.s) | 3194, 2963, 1660 1616, 1478, 1426 1370, 1277, 1155 1083, 894, 781 (KBr) | 91 | (structure with NC$_4$H$_9{}^n$) |
| 21 | Colorless needle crystals 176.0–179.0° C. (chloroform-hexane) | 2.74(2H, m), 3.67(2H, m), 4.87(2H, s) 6.77(1H, m), 6.89(1H, t, J=2.6Hz) 7.22–7.44(5H, m), 11.24(1H, br.) | 3420, 1665, 1620 1480, 1365, 1075 1025 | 47 | (structure with N—CH$_2$—phenyl) |
| 22 | Colorless prism crystals 77.0–78.0° C. (ethyl acetate-hexane) | 1.79(2H, m), 1.98(2H, m), 2.83(2H, m) 3.42–3.67(4H, m), 4.42(2H, t, J=7.0Hz) 6.74(1H, d, J=3.0Hz), 6.85(1H, d, J=3.0Hz) 7.10(1H, br.t) | 3415, 2940, 1650 1480, 1465, 1430 1375, 1315, 1120 | 77 | (structure with NH, (CH$_2$)$_4$Cl) |
| 23 | Colorless prism crystals 59.0–60.5° C. (ethyl acetate-hexane) | 1.80(2H, m), 1.98(2H, m), 2.79(2H, m) 3.21(3H, s), 3.54(2H, t, J=6.6Hz) 3.71(2H, m), 4.36(2H, t, J=7.2Hz) 6.65(1H, d, J=2.6Hz), 6.80(1H, d, J=2.6Hz) | 2945, 1660, 1635 1520, 1485, 1435 1395, 1375, 1325 1295, 1110, 1075 910 | 97 | (structure with NCH$_3$, (CH$_2$)$_4$Cl) |
| 24 | Colorless solid | 1.80–2.07(4H, m), 2.79(2H, m), 3.21(3H, s) 3.40(2H, t, J=6.3Hz), 3.72(2H, m) 4.36(2H, t, J=7.0Hz), 6.65(1H, d, J=2.6Hz) 6.80(1H, d, J=2.6Hz) | 2925, 1655, 1630 1480, 1395, 1320 1110, 1085, 905 | 43 | (structure with NCH$_3$, (CH$_2$)$_4$Br) |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 25 | Yellow crystals | 2.75–2.85(2H, m), 3.20(3H, s) 3.65–3.78(2H, m), 4.19(2H, d, J=6Hz) 5.08(2H, d, J=6Hz), 5.70–5.92(2H, m) 6.67(1H, d, J=3Hz), 6.83(1H, d, J=3Hz) | 1660, 1630 | 21 | (structure with NCH$_3$, CH$_2$CH=CHCH$_2$Cl (X)) |
| 26 | Pale yellow oil | 2.75–2.85(2H, m), 3.20(3H, s) 3.65–3.78(2H, m), 4.04(2H, d, J=6Hz) 4.97(2H, d, J=6Hz), 5.60–6.08(2H, m) 6.67(1H, d, J=3Hz), 6.80(1H, d, J=3Hz) | 1655, 1630 | 43 | (structure with NCH$_3$, CH$_2$CH=CHCH$_2$Cl (E)) |
| 27 | Pale yellow oil | 2.80(2H, m), 3.21(3H, s), 3.74(2H, m) 4.17(2H, t, J=2Hz), 5.26(2H, t, J=2Hz) 6.68(1H, d, J=3Hz), 7.06(1H, d, J=3Hz) | 1660, 1625 | 46 | (structure with NCH$_3$, CH$_2$C≡CCH$_2$Cl) |
| 28 | Colorless needle crystals 85.0–87.0° C. (ethyl acetate) | 2.32(2H, m), 2.80(2H, t, J=6.0Hz), 3.21(3H, s) 3.53(2H, t, J=6.0Hz), 3.71(2H, m) 4.48(2H, t, J=6.6Hz), 6.67(1H, d, J=2.7Hz) 6.86(1H, d, J=2.7Hz) | 2950, 1660, 1640 1485, 1440, 1400 1380, 1325, 1285 1145, 1120, 1080 920 | 85 | (structure with NCH$_3$, (CH$_2$)$_3$Cl) |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 29 | Colorless oil | 1.47(2H, m), 1.75–1.90(4H, m), 2.77(2H, dd, J=3.9, 6.6Hz), 3.21(3H, s), 3.53(2H, t, J=6.6Hz), 3.71(2H, m), 4.33(2H, t, J=7.3Hz), 6.64(1H, d, J=2.7Hz), 6.79(1H, d, J=2.7Hz) | 2950, 1660, 1640 1490, 1440, 1400 1380, 1325, 1120 1080, 920 | 90 | NCH₃ ring with N–(CH₂)₅–Cl |
| 30 | Colorless needle crystals 58.0–59.0° C. (diisopropyl ether) | 1.25(3H, t, J=7.0Hz), 1.80(2H, m), 1.97(2H, m), 2.79(2H, m), 3.53(2H, t, J=6.6Hz), 3.57–3.77(4H, m), 4.38(2H, t, J=7.3Hz), 6.64(1H, d, J=3.3Hz), 6.80(1H, d, J=3.3Hz) | 2930, 1655, 1625 1480, 1430, 1390 1375, 1300, 1135 1110, 910 | 94 | NC₂H₅ ring with N–(CH₂)₄–Cl |
| 31 | Colorless oil | 0.98(3H, t, J=7.3Hz), 1.66(2H, m), 1.81(2H, m), 1.96(2H, m), 2.78(2H, m), 3.50–3.58(4H, m), 3.68(2H, m), 4.37(2H, t, J=7.3Hz), 6.64(1H, d, J=3.0Hz), 6.80(1H, d, J=3.0Hz) | 2940, 1660, 1630 1480, 1430, 1180 1270, 1140, 1120 930, 895 | 98 | NC₃H₇ ring with N–(CH₂)₄–Cl |
| 32 | Colorless oil | 1.22(6H, d, J=7.3Hz), 1.77(2H, m), 1.97(2H, m), 2.75(2H, m), 3.50–3.59(4H, m), 4.38(2H, t, J=7.0Hz), 5.04(1H, m), 6.64(1H, d, J=3.0Hz), 6.79(1H, d, J=3.0Hz) | 2950, 1660, 1630 1480, 1460, 1440 1380, 1320, 1140 1080, 895 | 88 | N–C₃H₇$^i$ ring with N–(CH₂)₄–Cl |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 33 | Colorless oil | 0.97(3H, t, J=7.2Hz), 1.42(2H, m) 1.62(2H, m), 1.81(2H, m), 1.96(2H, m) 2.78(2H, m), 3.52(2H, t, J=6.5Hz) 3.58(2H, m), 3.59(2H, t, J=7.2Hz) 4.37(2H, t, J=7.3Hz), 6.65(1H, d, J=3.0Hz) 6.79(1H, d, J=3.0Hz) | 2957, 1662, 1632 1486, 1433, 1375 1241, 1209, 910 781 (film) | 98 | structure with NC$_4$H$_9^n$ and (CH$_2$)$_4$Cl |
| 34 | Colorless oil | 1.82(2H, m), 2.00(2H, m), 2.63(2H, m) 3.56(2H, t, J=6.6Hz), 3.65(2H, m) 4.43(2H, t, J=7.0Hz), 4.80(2H, s) 6.65(1H, d, J=2.7Hz), 6.82(1H, d, J=2.7Hz) 7.28-7.42(5H, m) | 2920, 1655, 1625 1475, 1420, 1395 1370, 1135, 980 | 96 | structure with NCH$_2$Ph and (CH$_2$)$_4$Cl |
| 35 | Colorless oil | 1.75-2.08(4H, m), 2.62(2H, m) 3.38(2H, t, J=6.3Hz), 3.65(2H, m) 4.43(2H, t, J=6.9Hz), 4.80(2H, s) 6.65(1H, d, J=2.6Hz), 6.82(1H, d, J=2.6Hz) 7.20-7.45(5H, m) | 2900, 1655, 1625 1475, 1370, 980 | 63 | structure with NCH$_2$Ph and (CH$_2$)$_4$Br |
| 36 | Colorless plate crystals 158.5-159.5° C. (chloroform-hexane) | 1.77(2H, m), 1.93(2H, m), 2.97(2H, m) 3.42(2H, m), 3.52(2H, t, J=7.0Hz) 4.35(2H, t, J=7.0Hz), 6.44(1H, d, J=2.7Hz) 6.82(1H, d, J=2.7Hz), 7.06(1H, d, J=5.9Hz) 9.89(1H, s) | 3570, 3415, 1645 1497, 1460, 1350 995, 940 | 87 | structure with HON, NH and (CH$_2$)$_4$Cl |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 37 | Colorless prism crystals 158.0–161.0° C. (ethyl acetate) | 2.28(2H, m), 2.98(2H, m), 3.13(3H, s) 3.51(2H, t, J=6.6Hz), 3.57(2H, m) 4.42(2H, t, J=6.6Hz), 6.40(1H, d, J=3.0Hz) 6.82(1H, d, J=3.0Hz), 7.94(1H, br.s) | 3580, 1635, 1480 1440, 1400, 1365 1350, 1080, 1000 960, 940, 900 | 86 | HON, NCH₃, (CH₂)₃Cl |
| 38 | Colorless needle crystals 113.0–114.0° C. (ethyl acetate) | 1.77(2H, m), 1.93(2H, m), 2.98(2H, m) 3.13(3H, s), 3.51(2H, t, J=6.3Hz) 3.58(2H, m), 4.31(2H, t, J=6.9Hz) 6.39(1H, d, J=2.6Hz), 6.76(1H, d, J=2.6Hz) 9.33(1H, br.s) | 3555, 3250, 2930 1620, 1475, 1395 1360, 960, 940 | 90 | HON, NCH₃, (CH₂)₄Cl |
| 39 | brown oil | 1.78(2H, m), 1.93(2H, m), 2.90(2H, m) 3.11(3H, s), 3.49–3.56(4H, m) 3.94(3H, s), 4.30(2H, t, J=7.2Hz) 6.43(1H, d, J=3.0Hz), 6.76(1H, d, J=3.0Hz) | 2950, 1630, 1485 1450, 1410, 1370 1050, 940, 880 850 | 47 | H₃CON, NCH₃, (CH₂)₄Cl |
| 40 | Colorless prism crystals 62.0–64.0° C. (isopropyl ether) | 1.76(2H, m), 1.97(2H, m), 2.94(2H, m) 3.10(3H, s), 3.46–3.59(4H, m) 4.30(2H, t, J=6.9Hz), 5.18(2H, s) 6.43(1H, d, J=3.0Hz) 6.75(1H, d, J=3.0Hz) 7.26–7.45(5H, m) | 2933, 1626, 1530 1487, 1483, 1367 1245, 1077, 1021 942, 774, 703 (KBr) | 87 | NOCH₂Ph, NCH₃, (CH₂)₄Cl |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 41 | Colorless solid | 1.78–2.03(4H, m), 2.98(2H, m), 3.13(3H, s) 3.39(2H, t, J=6.3Hz), 3.58(2H, m) 4.31(2H, t, J=6.6Hz), 6.39(1H, d, J=3.0Hz) 6.77(1H, d, J=3.0Hz), 8.95(1H, br.) | 3570, 2940, 1625 1480, 1435, 1400 1360, 1075, 995 960, 940 | 26 | HON, NCH₃, N(CH₂)₄Br |
| 42 | Colorless plate crystals 113.0–115.0° C. (ethyl acetate) | 1.44(2H, m), 1.73–1.86(4H, m), 2.97(2H, m) 3.13(3H, s), 3.52(2H, t, J=6.6Hz) 3.58(2H, m), 4.28(2H, t, J=7.3Hz) 6.38(1H, d, J=2.6Hz), 6.76(1H, d, J=2.6Hz) 8.55(1H, br.s) | 3570, 1620, 1480 1440, 1400, 1360 1350, 1080, 1000 960, 940, 900 | 87 | HON, NCH₃, N(CH₂)₅Cl |
| 43 | Colorless oil | 1.23(3H, t, J=7.0Hz), 1.75(2H, m) 1.91(2H, m), 2.99(2H, m), 3.40–3.68(6H, m) 4.32(2H, t, J=7.2Hz), 6.39(1H, d, J=3.3Hz) 6.75(1H, d, J=3.3Hz), 9.56(1H, br.s) | 3570, 3250, 2940 1625, 1475, 1435 1370, 1300, 990 950 | quantitative | HON, NC₂H₅, N(CH₂)₄Cl |
| 44 | Colorless needle crystals 93.0–95.0° C. ethanol-diisopropyl ether | 0.96(3H, t, J=7.3Hz), 1.56–1.85(4H, m) 1.93(2H, m), 2.97(2H, t, J=7.2Hz), 3.43–3.63(6H, m) 4.32(2H, t, J=7.2Hz), 6.39(1H, d, J=2.7Hz) 6.76(1H, d, J=2.7Hz), 8.54(1H, br.s) | 3560, 2930, 1620 1470, 1430, 1370 1100, 1000, 960 915 | 64 | HON, NC₃H₇, N(CH₂)₄Cl |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 45 | Colorless needle crystals 111.0–113.0° C. (diisopropyl ether) | 1.20(6H, t, J=6.6Hz), 1.74(2H, m) 1.89(2H, m), 2.93(2H, m), 3.46(2H, m) 3.50(2H, t, J=6.6Hz), 4.33(2H, t, J=6.6Hz) 4.93(1H, m), 6.38(1H, d, J=3.0Hz) 6.76(1H, d, J=3.0Hz), 8.52(1H, br.s) | 3570, 2930, 1610 1430, 1370, 1340 1165, 1000, 995 910, 870 | 68 | (structure with N–C$_3$H$_7^i$, HON, (CH$_2$)$_4$Cl) |
| 46 | Pale brown needle crystals 133.0–136.0° C. (ethanol) | 0.96(3H, t, J=7.3Hz), 1.39(2H, m) 1.61(2H, m), 1.78(2H, m), 1.92(2H, m) 2.96(2H, m), 3.50(4H, t, J=6.6Hz) 3.54(2H, m), 4.32(2H, t, J=6.6Hz) 6.38(1H, d, J=2.6Hz) 6.75(1H, d, J=2.6Hz), 7.26(1H, br.s) | 3250, 2952, 1610 1530, 1483, 1441 1368, 1242, 1005 940, 780 (KBr) | 86 | (structure with NC$_4$H$_9^n$, NOH, (CH$_2$)$_4$Cl) |
| 47 | Colorless prism crystals 160.0–162.0° C. (chloroform-hexane) | 1.80(2H, m), 1.95(2H, m), 2.82(2H, m) 3.42–3.61(4H, m), 4.37(2H, t, J=7.0Hz) 4.73(2H, s), 6.39(1H, d, J=2.7Hz) 6.78(1H, d, J=2.7Hz), 7.25–7.42(5H, m) 8.87(1H, br.s) | 3560, 1620, 1465 1420, 1350, 1045 | 96 | (structure with NCH$_2$–phenyl, HON, (CH$_2$)$_4$Cl) |
| 48 | Colorless oil | 1.50–1.70(2H, m), 1.70–1.98(6H, m) 2.06(2H, m), 2.35–2.59(3H, m) 2.62(2H, m), 3.04(2H, m), 3.66(2H, m) 4.42(2H, t, J=7.3Hz), 4.81(2H, s) 6.65(1H, d, J=2.6Hz), 6.85(1H, d, J=2.6Hz) 7.12–7.42(10H, m) | 2930, 1660, 1630 1485, 1435, 1375 1030 | 27 | (structure with NCH$_2$–phenyl, O=, (CH$_2$)$_4$–N–4-phenylpiperidine) |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 49 | Pale yellow oil | 1.56(2H, m), 1.69-1.93(6H, m), 2.04(2H, dt, J=11.2Hz, 4.0Hz), 2.40(2H, m), 2.49(1H, m), 2.79(2H, m), 3.02(2H, m), 3.21(3H, s), 3.71(2H, m), 4.35(2H, t, J=7.2Hz), 6.64(1H, d, J=2.6Hz), 6.81(1H, d, J=2.6Hz), 7.13-7.35(5H, m) | 2930, 1655, 1635 1480, 1390, 1370 1320, 1140, 1105 905 | 94 | |
| 50 | Pale yellow plate crystals 208.0-210.0° C. (isopropanol-diisopropyl ether) | 1.85-2.18(8H, m), 2.45-2.93(5H, m), 3.04(2H, m), 3.21(3H, s), 3.52-3.82(4H, m), 4.32(2H, t, J=7.2Hz), 6.66(1H, m), 6.86(1H, m), 7.17-7.42(5H, m), 12.03(1H, br.) | (KBr) 3430, 2935, 1655 1620, 1525, 1480 1440, 1400, 1190 1140, 945, 905 | — | |
| 51 | Colorless prism crystals 164.0-165.0° C. (isopropanol-diethyl ether) | 1.54(2H, m), 1.65-1.95(6H, m), 2.04(2H, m), 2.39(2H, m), 2.49(1H, m), 2.95(2H, m), 3.04(2H, m), 3.12(3H, s), 3.56(2H, m), 4.30(2H, t, J=7.3Hz), 6.35(1H, d, J=2.6Hz), 6.76(1H, d, J=2.6Hz), 7.13-7.35(5H, m), 9.22(1H, br.s) | 3550, 2925, 1620 1475, 1390, 1355 1340, 1145, 1110 1060, 950, 935 | 89 | |
| 52 | Yellow oil | 1.35(2H, m), 1.44-1.70(5H, m), 1.70-1.98(4H, m), 2.32(2H, t, J=7.6Hz), 2.53(2H, d, J=6.6Hz), 2.78(2H, m), 2.89(2H, m), 3.20(3H, s), 3.70(2H, m), 4.32(2H, t, J=7.3Hz), 6.62(1H, d, J=2.6Hz), 6.78(1H, d, J=2.6Hz), 7.07-7.35(5H, m) | 2910, 1650, 1625 1475, 1385, 1310 1135, 1100, 1065 960, 940 | 65 | |

TABLE 1-continued
| Comp'd No. | Property Melting point (recrystallization solvent) | NMR[1] ($\delta$ ppm 270 MHz) | IR[2] ($cm^{-1}$) | Yield (%) | Structural formula |
|---|---|---|---|---|---|
| 53 | Pale yellow oil | 1.45–1.62(2H, m), 1.75–1.90(2H, m) 2.20–2.55(10H, m), 2.72–2.85(2H, m) 3.20(3H, s), 3.60–3.78(2H, m) 4.33(2H, t, J=7Hz), 6.62(1H, d, J=3Hz) 6.78(1H, d, J=3Hz), 6.85–7.15(8H, m) | 1655, 1630 | 37 | 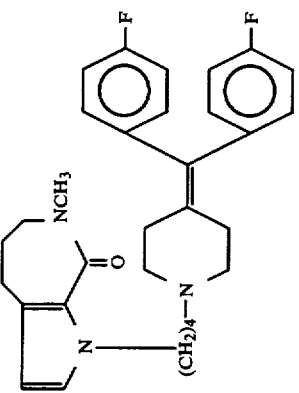 |
| 54 | Pale yellow oil | 1.40–1.60(4H, m), 1.65–2.05(4H, m) 2.25–2.45(3H, m), 2.45–2.68(2H, br.s) 2.70–2.82(2H, m), 2.85–3.03(2H, m) 3.18(3H, s) 3.56–3.78(2H, m), 4.30(2H, t, J=6Hz) 6.61(1H, d, J=3Hz), 6.78(1H, d, J=3Hz) 6.88–7.08(4H, m), 7.30–7.55(4H, m) | 1655, 1630 | 45 | 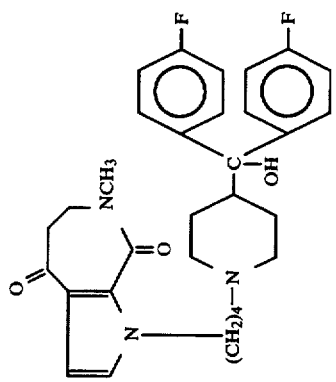 |
| 55 | pale yellow oil | 1.42–1.58(2H, m), 1.62–1.98(6H, m) 2.06–2.22(2H, m), 2.28–2.40(2H, m) 2.66–2.82(4H, m), 3.19(3H, s) 3.38–3.50(1H, m), 3.64–3.75(2H, m) 4.32(2H, t, J=6Hz), 5.50(1H, s) 6.62(1H, d, J=3Hz), 6.78(1H, d, J=3Hz) 7.18–7.40(10H, m) | 1650, 1625 | 61 | 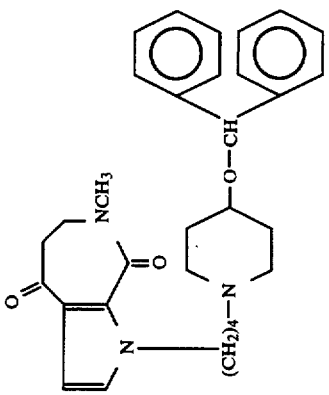 |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 56 | Colorless oil Hydrochloride: Colorless plate crystals 196–200° C. | 1.47–1.63(2H, m), 1.79–1.93(2H, m) 2.02–2.16(4H, m), 2.38–2.55(4H, m) 2.79(2H, m), 2.98(2H, m), 3.21(3H, s) 3.72(2H, m), 4.36(2H, t, J=7.3Hz) 6.65(1H, d, J=3.3Hz), 6.80(1H, d, J=3.3Hz) 7.28–7.53(5H, m) | 2940, 2240, 1660 1635, 1485, 1395 910 | 70 | (structure: pyrrole fused ketone with NCH₃ amide, linked via (CH₂)₄ to 4-cyano-4-phenylpiperidine) |
| 57 | Colorless needle crystals 166.0–168.0° C. (ethanol) | 1.45–1.63(2H,m), 1.73–1.88(2H, m) 2.05–2.22(4H, m), 2.40–2.55(4H, m) 2.90–3.05(4H, s), 3.13(3H, s), 3.58(2H, m) 4.31(2H, t, J=7.3Hz), 6.36(1H, d, J=2.6Hz) 6.77(1H, d, J=2.6Hz), 7.30–7.55(5H, m) 8.50(1H, br.s) | 3570, 2940, 2240 1625, 1480, 1400 945, 905 | 61 | (structure: oxime HON= variant of compound 56) |
| 58 | Brown oil | 1.80–1.90(4H, m), 1.95–2.20(4H, m) 2.34(2H, m), 2.78(2H, m), 2.92–3.02(2H, m) 3.21(3H, s), 3.15–3.27(1H, m), 3.71(2H, m) 4.38(2H, m), 6.63(1H, d, J=3.0Hz) 6.84(1H, d, J=3.0Hz), 7.14(2H, t, J=8.6Hz) 7.96(2H, m) | 2940, 1680, 1600 1635, 1660, 1480 1395, 1375, 1320 1155, 975, 910 | 33 | (structure: pyrrole fused ketone with NCH₃ amide, linked via (CH₂)₃ to 4-(4-fluorobenzoyl)piperidine) |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 59 | Colorless needle crystals 194.0–197.0° C. (methanol) | 1.77–1.95(4H, m), 1.90–2.18(4H, m) 2.36(2H, t, J=7.3Hz), 2.90–3.02(4H, m) 3.12(3H, s), 3.20(1H, m), 3.55(2H, m) 4.31(2H, m), 6.35(1H, d, J=2.6Hz) 6.78(1H, d, J=2.6Hz), 7.13(2H, t, J=8.6Hz) 7.95(2H, m), 10.10(1H, br.s) | 3570, 2940, 1680 1625, 1600, 1480 1400, 1350, 1160 975, 900 | 69 | |
| 60 | Pale yellow oil | 1.53(2H, m), 1.72–1.92(6H,m) 1.97–2.17(2H, m), 2.38(2H, t, J=7.3Hz) 2.77(2H, m), 2.96(2H, m) 3.10–3.30(4H, m, s at 3.21), 3.72(2H, m) 4.35(2H, t, J=7.3Hz), 6.63(1H, d, J=2.6Hz) 6.80(1H, d, J=2.6Hz), 7.13(2H, t, J=8.6Hz), 7.96(2H, m) | 2930, 1660, 1635 1600, 1485, 1395 1155, 975 | 86 | |
| 61 | Colorless needle crystals 166.0–168.0° C. (isopropanol) | 1.54(2H, m), 1.67–2.00(6H, m), 2.13(2H, m) 2.40(2H, t, J=7.6Hz), 2.80–3.08(4H, m) 3.12(3H, s), 3.21(1H, quint., J=7.3Hz) 3.56(2H, m), 4.28(2H, t, J=6.9Hz) 6.35(1H, d, J=2.6Hz), 6.75(1H, d, J=2.6Hz) 7.13(2H, t, J=6.9Hz) 7.96(2H, dd, J=8.6Hz, 5.6Hz) 10.16(1H, br.s) | 3550, 2925, 1675 1615, 1590, 1470 1390, 1145, 965 935 | 72 | |

TABLE 1-continued

| Comp'd No. | Property Melting point (recrystallization solvent) | NMR[1] (δ ppm 270 MHz) | IR[2] (cm$^{-1}$) | Yield (%) | Structural formula |
|---|---|---|---|---|---|
| 62 | Colorless needle crystals 197.0–198.0° C. (ethanol) | (DMSO-d$_6$/TMS) 1.05–2.10(8H, m), 2.29(3H, s), 2.81(2H, m) 2.95–3.20(4H, m), 3.02(3H, s) 3.40–3.60(4H, m), 3.72(1H, m), 4.23(2H, m) 6.28(1H, d, J=2.6Hz), 7.04(1H, d, J=2.6Hz) 7.11(2H, d, J=7.9Hz), 7.38(2H, m) 7.50(2H, d, J=7.9Hz), 8.10(2H, m) 8.98(1H, br.s), 10.95(1H, s) | 3182, 3029, 1672 1598, 1538, 1496 1439, 1404, 1233 1163, 1116, 1011 947, 678 (KBr) | — | |

[1] Measured in CDCl$_3$/TMS unless otherwise specifically indicated.
[2] Measured as chloroform solution unless otherwise specifically indicated.

Test

With respect to the compounds of the present invention, their anti-$\alpha_1$ action and anti-serotonin action were investigated by the testing methods which will be described below. The test results of some representative compounds are summarized in Table 2.

(1) Anti-$\alpha_1$ action

The thoracic aorta of each Hartley male guinea pig (body weight: 300–500 g) was excised. The sample cut in a helical form was suspended under 1 g load in a Magnus cylinder filled with the Tyrode solution of 37° C. which had been saturated with a mixed gas consisting of 95% $O_2$+5 $CO_2$. Using an isometric transducer (TB-612J/NIHON KOHDEN) and a pressure preamplifier (AP-620G/NIHON KOHDEN), variations in tension were measured. The measurement results were recorded on a thermal pen-writing recorder (WT-647G/NIHON KOHDEN). Taking the tonic contraction induced by $10^{-5}$M norepinephrine (NE) as 100%, the percent contractions upon addition of each test drug at $10^{-8}$ and $10^{-7}$M were determined as anti-$\alpha_1$ action.

(2) Anti-serotonin action (anti-5-HT action)

The superior mesenteric artery of each Hartley male guinea pig (body weight: 300–500 g) was excised. The sample cut in a helical form was suspended under 0.3 g load in a Magnus cylinder filled with the Tyrode solution of 37° C. which had been saturated with a mixed gas consisting of 5% $CO_2$+95% $O_2$. Using an isometric transducer (UL-10/SHINKOH K.K.) and a pressure preamplifier (DSA-605A/SHINKOH K.K.), variations in tension were measured. The measurement results were recorded on a pen-writing recorder (VP-6537A/NATIONAL K.K.). Taking the phasic contraction induced by $10^{-5}$M serotonin as 100%, the percent contractions in the presence of each test drug at $10^{-7}$ and $10^{-6}$M were determined as anti-5-HT action.

TABLE 2

| Comp'd No. | Form | Anti $\alpha_1$ action (% of Control) | | Anti 5-HT action (% of Control) | |
|---|---|---|---|---|---|
| | | $10^{-8}$M | $10^{-7}$M | $10^{-7}$M | $10^{-6}$M |
| 48 | Free | 77.4 | 37.7 | 88.0 | 49.0 |
| 51 | Free | 74.9 | 30.8 | 84.4 | 54.4 |
| 54 | Hydrochloride | 90.4 | 26.0 | 62.9 | 14.7 |
| 60 | Hydrochloride | 43.9 | 20.5 | 62.9 | 11.8 |
| 61 | Free | 44.7 | 21.4 | 12.1 | 4.1 |
| 62 | P-toluenesulfonate | 26.8 | 17.1 | 47.4 | 8.2 |
| 65 | Free | 19.5 | 9.9 | 19.9 | 3.6 |
| 66 | Free | 19.3 | 10.4 | 77.6 | 6.9 |
| 75 | Free | 37.0 | 17.9 | 12.9 | 8.2 |
| 81 | Free | 57.5 | 28.9 | 57.1 | 14.3 |
| 84 | Free | 86.5 | 67.0 | 60.0 | 3.8 |
| 91 | Free | 58.2 | 35.5 | 16.1 | 10.3 |
| 92 | Free | 49.3 | 21.5 | 48.5 | 12.5 |

We claim:

1. A pyrroloazepine derivative represented by the following formula (I):

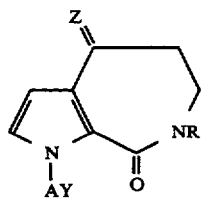

wherein R means a hydrogen atom, a linear or branched $C_{1-6}$ alkyl group or a $C_{7-10}$ aralkyl group, A denotes a linear or branched $C_{2-10}$ alkylene, alkenylene or alkynylene group, Z stands for O, $NOR_1$ in which $R_1$ is a hydrogen atom or an alkyl, aryl or aralkyl group, or $NOCOR_5$ in which $R_5$ is a hydrogen atom or an alkyl, aryl or aralkyl group, and Y means a group

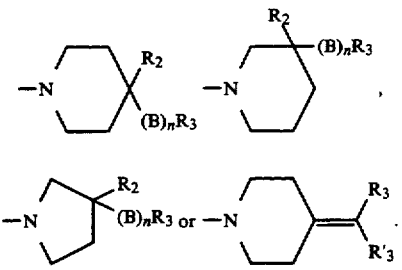

$R_2$ means a hydrogen atom or a cyano group, $R_3$ and $R'_3$ may be the same or different and individually denote a substituted or unsubstituted phenyl group or a substituted or unsubstituted aralkyl group, and B is an oxygen atom, sulfur atom or a carbonyl group, sulfinyl group, sulfonyl group, a substituted or unsubstituted cyclic or acyclic acetal group or a hydroxymethylene group which may be substituted at the carbon atom thereof by a substituent selected from the group consisting of lower alkyl, phenyl and phenyl substituted by at least one halogen atom or $C_{1-4}$ alkoxy group; and n stands for 0 or 1; or a salt thereof.

2. The pyrroloazepine derivative of claim 1, wherein in the formula (I), Y is the group

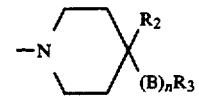

in which B, $R_2$, $R_3$ and n have the same meanings as defined above, or a salt thereof.

3. The pyrroloazepine derivative of claim 1, wherein in the formula (I), Z is O or NOH, or a salt thereof.

4. An intermediate suitable for use in the production of a pharmaceutical product, said intermediate being represented by the following formula (III):

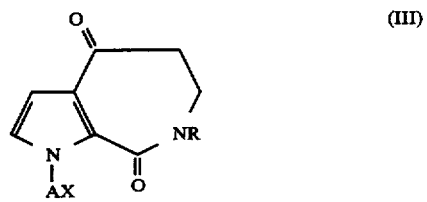

(III)

wherein A denotes a linear or branched $C_{2-10}$ alkylene, alkenylene or alkynylene group, R means a hydrogen atom, a linear or branched $C_{1-6}$ alkyl group or a $C_{7-10}$ aralkyl group, and X represents a substituent selected from the group consisting of halogen, methanesulfonyl and p-toluenesulfonyl.

5. An intermediate suitable for use in the production of a pharmaceutical product, said intermediate being represented by the following formula (X):

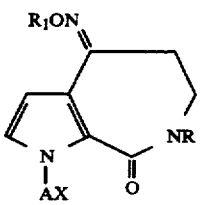

(X)

wherein A denotes a linear or branched $C_{2-10}$ alkylene, alkenylene or alkynylene group, R means a hydrogen atom, a linear or branched $C_{1-6}$ alkyl group or a $C_{7-10}$ aralkyl group, $R_1$ is a hydrogen atom or an alkyl, aryl or aralkyl group, and X represents a substituent selected from the group consisting of halogen, methanesulfonyl and p-toluenesulfonyl.

6. An intermediate suitable for use in the production of a pharmaceutical product, said intermediate being represented by the following formula (XII):

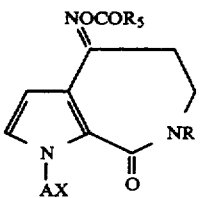

(XII)

wherein A denotes a linear or branched $C_{2-10}$ alkylene, alkenylene or alkynylene group, R means a hydrogen atom, a linear or branched $C_{1-6}$ alkyl group or a $C_{7-10}$ aralkyl group, $R_5$ is a hydrogen atom or an alkyl, aryl or aralkyl group, and X represents a substituent selected from the group consisting of halogen, methanesulfonyl and p-toluenesulfonyl.

7. A therapeutic agent for circulatory disease having anti-$\alpha_1$ activity and anti-serotonin activity comprising: (a) an effective amount of the pyrroloazepine derivative (I) or a pharmacologically acceptable salt thereof as described in claim 1 and (b) a pharmaceutically acceptable carrier.

8. The pyrroloazepine derivative of claim 1, wherein in the formula (I), A denotes a linear or branched $C_{2-10}$ alkylene group.

9. An intermediate suitable for use in the production of a pharmaceutical product, said intermediate being represented by the following formula (II'):

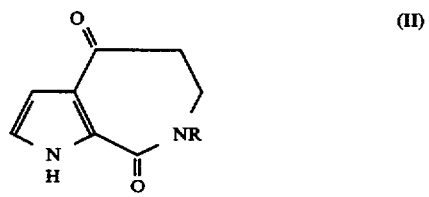

(II)

wherein R' means a linear or branched $C_{1-6}$ alkyl group or a $C_{7-10}$ aralkyl group.

* * * * *

UNITED STATES PATENT AND TRADEMARK OFFICE
CERTIFICATE OF CORRECTION

PATENT NO.   : 5,416,082
DATED        : May 16, 1995
INVENTOR(S)  : Akira MIZUNO, et al.

It is certified that error appears in the above-indentified patent and that said Letters Patent is hereby corrected as shown below:

On the title page, Item [75], the fifth inventor's city should read:

--Takatsuki--

On the title page, Item [*], the Terminal Disclaimer Date should read:

--Apr. 27, 2010--

Signed and Sealed this

Eighteenth Day of July, 1995

Attest:

BRUCE LEHMAN

*Attesting Officer*     *Commissioner of Patents and Trademarks*